United States Patent
Lewis et al.

(10) Patent No.: US 9,895,420 B2
(45) Date of Patent: Feb. 20, 2018

(54) IL-1BETA PROPEPTIDE AND IL-1RA CHIMERA AND METHODS OF USING THE SAME

(71) Applicants: B.G. NEGEV TECHNOLOGIES AND APPLICATIONS LTD., AT BEN GURION UNIVERSITY, Beer Sheva (IL); THE REGENTS OF THE UNIVERSITY OF COLORADO, A BODY CORPORATE, Denver, CO (US)

(72) Inventors: Eli Lewis, Beer Sheva (IL); Peleg Rider, Beer Sheva (IL); Charles A. Dinarello, Boulder, CO (US)

(73) Assignees: B.G. NEGEV TECHNOLOGIES AND APPLICATIONS LTD., AT BEN GURION UNIVERSITY, Beer Sheva (IL); THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 14/894,945

(22) PCT Filed: Jun. 5, 2014

(86) PCT No.: PCT/IL2014/050508
§ 371 (c)(1),
(2) Date: Nov. 30, 2015

(87) PCT Pub. No.: WO2014/195953
PCT Pub. Date: Dec. 11, 2014

(65) Prior Publication Data
US 2016/0220641 A1 Aug. 4, 2016

Related U.S. Application Data

(60) Provisional application No. 61/831,318, filed on Jun. 5, 2013.

(51) Int. Cl.
| | | |
|---|---|---|
| C07K 19/00 | (2006.01) | |
| A61K 38/20 | (2006.01) | |
| C07K 14/545 | (2006.01) | |
| C07K 14/715 | (2006.01) | |
| A61K 38/17 | (2006.01) | |
| C07K 14/47 | (2006.01) | |

(52) U.S. Cl.
CPC ...... *A61K 38/2006* (2013.01); *A61K 38/1709* (2013.01); *C07K 14/47* (2013.01); *C07K 14/545* (2013.01); *C07K 14/7155* (2013.01); *C07K 2319/00* (2013.01); *C07K 2319/21* (2013.01); *C07K 2319/50* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 5,464,764 A | 11/1995 | Capecchi et al. | |
| 5,487,992 A | 1/1996 | Capecchi et al. | |
| 5,932,447 A | 8/1999 | Siegall | |

FOREIGN PATENT DOCUMENTS

| | | |
|---|---|---|
| WO | 03068934 | 8/2003 |
| WO | 2009077755 | 6/2009 |
| WO | 2011028344 | 3/2011 |
| WO | 2012016203 A1 | 2/2012 |

OTHER PUBLICATIONS

Peleg Rider et al: "IL-1 Receptor Antagonist Chimeric Protein: Context-Specific and Inflammation-Restricted Activation", The Journal of Immunology, vol. 195, No. 4, Jul. 8, 2015, pp. 1705-1712.
Dinarello C.A. "Interlukin-1, interlukin-1 receptors and interlukin-1 receptor antagonist", Int Rev. Immunol. 1998: 16(5-6) 457-99.
Hazuda D, Webb RL, Simon P, Young P. Purification and characterization of human recombinant precursor interleukin 1 beta. The Journal of biological chemistry. 1989;264(3)1689-93.
Hazuda DJ, Strickler J, Kueppers F, Simon PL, Young PR. Processing of precursor interleukin 1 beta and inflammatory disease. The Journal of biological chemistry. 1990;265(11):6318-22. Epub Apr. 15, 1990).
Dinarello CA, Simon A, van der Meer JW. Treating inflammation by blocking interleukin-1 in a broad spectrum of diseases. Nature reviews Drug discovery. 2012;11(8):633-52. Epub Aug. 2, 2012.

*Primary Examiner* — Dong Jiang
(74) *Attorney, Agent, or Firm* — The Roy Gross Law Firm, LLC; Roy Gross

(57) ABSTRACT

The present invention provides a chimera protein made of amino acid residues derived from IL-1beta propeptide and the IL-1Ra mature peptide and polynucleotides encoding the protein. The present invention also provides usages of the protein and the polynucleotides in pharmaceutical compositions that treat inflammation.

18 Claims, 10 Drawing Sheets

SEQ ID NO: 6
ATGGCAGAAGTACCTGAGCTCGCCAGTGAAAATGATGGCTTATTACAGTGGAATGAGGATGACTTGTTCTTTGAAGCTGATGGGCCTAAACAGATGAAGT    < 100
 M  A  E  V  P  E  L  A  S  E  N  M  A  Y  Y  S  G  N  E  D  D  L  F  F  E  A  D  G  P  K  Q  M  K  C

SEQ ID NO: 3
GCTTCTCAGGACCTGGACCTCTGCCCTCTGGATGGCGGGATCCAGCTACAGAGAATCTCGACACTACAGCGAAGGCTTCAGGCAGGCCGCGTCAGT     < 200
 S  F  Q  D  L  D  L  C  P  L  D  G  G  I  Q  L  R  I  S  D  H  Y  S  K  G  F  R  Q  A  A  S  V

TGTGTGGCCATGGACAAGCGGATGTTGGTTCCTTGCCCACAGACCTTCCAGGAGAATGACCTGAGCACGTTCTTTCCCTTCATCTTTGAAGAA     < 300
 V  V  A  M  D  K  R  M  L  V  P  C  P  Q  T  F  Q  E  N  D  L  S  T  F  F  P  F  I  F  E  E

GAACCTATCTTCTTCGACACATGGGATAACGAAGCTGTACATGATGCACCTGTACGAAAGCTTCGACCTAGTGGAAGAAATCCAGCAAGATGCAAG     < 400
 E  P  I  F  F  D  T  W  D  N  E  A  V  H  D  A  P  V  R  K  L  R  P  S  G  R  K  S  K  M  Q  A
                                                    Proteolytic sites - residues 103 to 120

CCTTCAGAATGTGGGATGTTAACCAGAAGACCTTCTATCTGAGGAACATGCAACTAGTTGCTGGATACTTGCAAGGACCAATGTCAATTTAGAAGAAAA   < 500
 F  R  I  W  D  V  N  Q  K  T  F  Y  L  R  N  M  Q  L  V  A  G  Y  L  Q  G  P  M  V  N  L  E  E  K

GATAGATGTGGTACCATTGAGCCTCATGCTCTGTTCTTGGGAATCCATGGAGGAAGATGCCTGTCTGGTTGTCAAGTCTGGTGATGAGAGACCTC     < 600
 I  D  V  V  P  I  E  P  H  A  L  F  L  G  I  H  G  G  K  M  C  L  S  C  V  K  S  G  D  E  T  R  L

CAGCTGGAGGCAGTAACATCACTGACCTCAGCGAGAACAGAAGCCTCGATCGCTTCATCCGCTCCAGACAGTGCCCACCAGTTTG     < 700
 Q  L  E  A  V  N  I  T  D  L  S  E  M  R  K  Q  D  K  R  F  A  I  R  S  D  S  G  P  T  S  E  E

AGTCTGCGCCTGGCCAGGGTTGTTCCCTCCACAGCGGATGGAAGCTGACCAGCCCGTCACCAATATGCCTGACGAAGGCGTCATGGTCACCAA     < 800
 S  A  A  C  P  G  W  F  L  C  T  A  M  E  A  D  Q  P  V  S  T  N  M  P  D  E  G  V  M  V  T  K

ATTCTACTTCCAGGAGGACGAGTAG     < 825
 F  Y  F  Q  E  D  E  *

Figure 1C

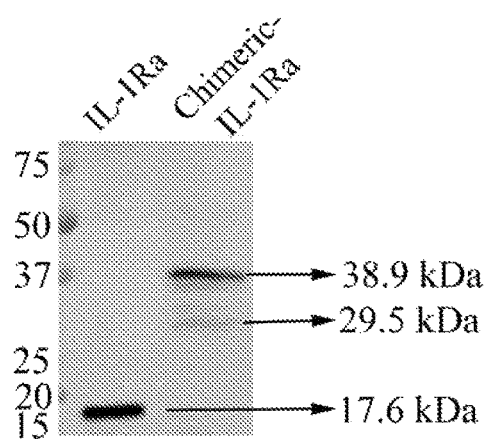
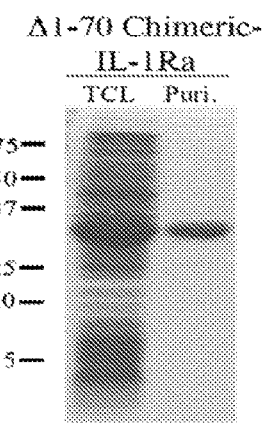
Figure 7A
Figure 7B
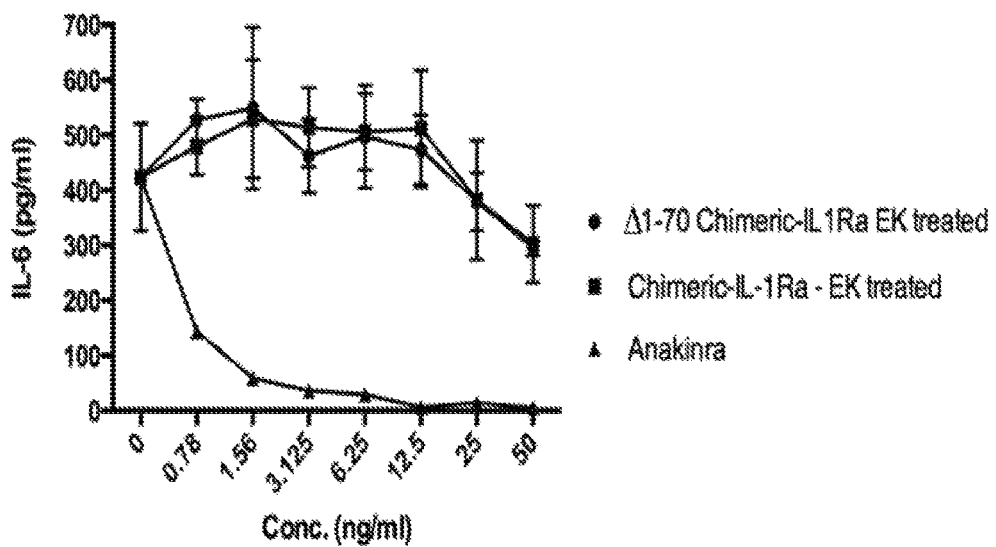
Figure 7C
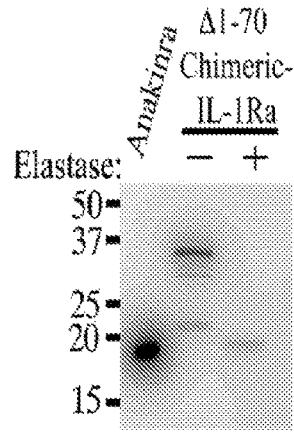
Figure 7D

IL-1BETA PROPEPTIDE AND IL-1RA CHIMERA AND METHODS OF USING THE SAME

CROSS REFERENCE TO RELATED APPLICATIONS

This patent application is a U.S. National Phase filing of commonly owned PCT Application No. PCT/IL2014/050508, filed Jun. 5, 2014, which is based on and claims the benefit of the filing date of U.S. Provisional Patent Application Ser. No. 61/831,318, filed Jun. 5, 2013, both which are incorporated herein by reference in their entirety.

FIELD OF INVENTION

This invention is directed to; inter alia, a chimeric protein comprising an amino acid sequence derived from IL-1beta propeptide and the IL-1Ra mature peptide and to usages of the protein in pharmaceutical compositions that treat inflammation.

BACKGROUND OF THE INVENTION

Reducing pain, inflammation, and fever with plant extracts (such as salicylate-containing plant extracts) can be traced throughout written human history. One hundred and fifty years ago, Felix Hoffman acetylated salicylic acid and created aspirin. Aspirin inhibits the cyclooxygenase (COX) enzymes COX-1 and COX-2, which synthesize inflammatory prostaglandins and thromboxanes. The ability to block inflammation via mediators such as prostaglandins and thromboxanes accounts for aspirin being the world's most used therapeutic agent.

Yet, it is still the challenge of the pharmaceutical chemist to develop more effective and less toxic agents to treat the signs and symptoms and development of acute inflammation as well as the long-term consequences of chronic inflammatory diseases Inflammation is a dynamic process with proinflammatory cytokines such as tumor necrosis factor (TNF)-a, interleukin (IL)-1b, and vascular endothelial growth factor (VEGF) playing central roles. A number of "biologicals" have been developed to treat inflammation, including agents that reduce the activity of specific cytokines or their receptors.

Neutralization of specific proinflammatory cytokines has "canonized" their causative role in inflammation and has changed the lives of millions of patients with these diseases. One drawback of anti-cytokine therapies is decreased host immune defense against infection and possibly cancer.

Many intracellular signaling molecules are involved in normal cellular functions and inflammation thus the effective concentration that does not elicit organ toxicity needs to be carefully determined.

Interleukin-1 (IL-1) is a potent pro-inflammatory cytokine that promotes chronic and acute inflammation, as well as harbors metabolic manifestations and is involved in hematopoiesis. IL-1 belongs to a large family of cytokines that consists of both pro-inflammatory and anti-inflammatory members; IL-1 receptor antagonist (IL-1Ra) is an anti-inflammatory IL-1 family member. IL-1alpha, IL-1beta and IL-1Ra, bind to the same receptor. The signaling receptor is IL-1R1. In order for signaling to occur, IL-1R1 requires a co-receptor, the IL-1R accessory protein (IL-1RAcP). Successful association with IL-1RAcP requires conformational changes that occur after IL-1 family members, IL-1α or IL-1β, bind to IL-1R1. However, binding to IL-1R1 at a higher affinity compared to IL-1α or IL-1β, IL-1Ra, IL-1Ra does not recruit IL-1RAcP, thus eliciting no inflammatory signal.

IL-1Ra may thus interfere with excessive IL-1 activities; IL-1 plays a critical role in many inflammatory diseases, such as gout, osteoarthritis and hypoxic tissue injury. However, IL-1 was also shown to be involved in non-classic inflammatory conditions, such as post-infarction cardiac failure, loss of beta cells during type 1 diabetes, elevated insulin resistance in type 2 diabetes and facilitation of tumor growth, angiogenesis and metastases. Both IL-1 alpha and IL-1beta are transcribed and translated as precursor proteins of 31 kDa. IL-1alpha can be found as a precursor or cleaved 17 kDa mature form. Precursor of IL-1alpha can be processed by the $Ca^{2+}$-dependent protease calpain, a process which is not common in all cells. The necessity of IL-1alpha cleavage is not fully understood since both forms of the molecule are active and can trigger IL-1R1 signaling. IL-1beta, unlike IL-1alpha is not present in cells under normal conditions, and it is rapidly upregulated upon recognition of bacterial products by TLR signaling. Moreover, unlike IL-1alpha, IL-1beta precursor is inactive, and multiple steps control its activation. Transcription and translation of IL-1beta are not sufficient for its activity; a cleavage step of the precursor into active mature form is required. The classic cleavage of IL-1beta protein is executed by the cysteine protease caspase-1, which itself requires activation by a multi-protein complex, the inflammasome. IL-1beta can be secreted by secretory lysosomes, which contains the cytokine together with its activating protease, caspase-1 to the surrounding environment.

However, IL-1beta can be released due to cell death and loss of membrane integrity, either as mature or in its un-cleaved precursor form. Although IL-1beta can trigger IL-1R1 and promote inflammation and fever only in its mature form, the precursor of IL-1beta can be activated in the inflammatory site due to elevated levels of inflammatory proteases. Tt has been demonstrated that recombinant IL-1beta precursor can be cleaved by elastase, cathepsin G, collagenase, proteinase-3, mast cell chymase and Natural Killer (NK)/cytotoxic T cell (TCL)-granzyme A (Hazuda D J, Strickler J, Kueppers F, Simon P L, Young P R. Processing of precursor interleukin 1 beta and inflammatory disease. The Journal of biological chemistry. 1990; 265(11):6318-22. Epub 1990/04/15).

Hazude et al. also sequenced the processed proteins sequences and found the site of cleavage. According to their data, cleavage site can vary from Ile 103 to Asp 116. Using EL4 cells stimulation assay, it was shown that the cleavage products are active compared to the inactive precursor. In addition, it was shown that the IL-1beta precursor can be cleaved following incubation with synovial fluids from polyarthritis patients or bronchoalveolar lavage (BAL) from sarcoidosis patients, emphysema or infection after lung transplantation patients.

Not only neutrophil proteases appear to digest IL-1beta precursor, mast cell chymase was also shown to liberate the propeptide of IL-1beta, and to activate the cytokine. Chymase is a chymotrypsin-like serine protease present in secretory granules of mast cells. It is capable of promoting matrix degradation and inflammation. The 18 kDa IL-1beta product is indeed active, comparable to the mature IL-1beta. Natural killer (NK) and Cytotoxic T cells (TCL) enzyme, granzyme A, can also cut IL-1beta, and the site of cleavage was demonstrated to be following Arg 120, four residues C-terminally to the caspase-1 site (Asp 116).

Anakinra is a recombinant, non-glycosylated form of IL-1Ra was shown to relieve disease severity in various auto-inflammatory diseases, such as rheumatoid arthritis, gout, osteoarthritis and more (Dinarello C A, Simon A, van der Meer J W. Treating inflammation by blocking interleukin-1 in a broad spectrum of diseases. Nature reviews Drug discovery. 2012; 11(8):633-52. Epub 2012/08/02). Anakinra has been approved by the FDA since 2001 for the treatment of rheumatoid arthritis and recently for the treatment of cryopyrin-associated periodic syndromes (CAPS), a group of inherited auto-inflammatory syndromes in which excess IL-1 mediates exacerbated inflammatory events. Administered either locally or systemically, Anakinra is limited by an extremely short half-life and bares the risk of excessive systemic IL-1 blockade.

There is a need for more effective means of anti-IL-1 therapy for treating inflammation, such as by using IL-1Ra that is not constitutively active (as in the case of Anakinra), but is activated only at sites of excessive inflammation.

SUMMARY OF THE INVENTION

The present invention provides, in some embodiments, chimeric polypeptides comprising IL-1Ra and the N-terminal peptide (NTP) of IL-1β or a fragment thereof, compositions comprising same and methods of use thereof, including but not limited to treatment of an inflammatory disease or disorder.

In one aspect, the present invention provides a protein comprising an amino acid sequence derived from IL-1beta propeptide and an IL-1Ra mature peptide or analogs thereof, wherein the amino acid sequence derived from IL-1beta propeptide comprises at least one protease cleavage site. In another embodiment, said amino acid sequence comprising at least one protease cleavage site comprises or consists of the amino acid sequence as set forth in PIFFDTWDNEAYVHDAPVR (SEQ ID NO: 13). In another embodiment, the at least one protease cleavage site is a serine protease cleavage site.

In one embodiment, the amino acid sequence derived from IL-1beta propeptide is an amino acid sequence derived or corresponding to IL-1beta N-terminal peptide (NTP). In another embodiment, said amino acid sequence comprises at least 35, at least 50, or at least 80 contiguous amino acid residues of IL-1beta propeptide.

In one embodiment, the present invention provides a protein comprising a linker, wherein the carboxy terminus of the linker is attached (i.e. contiguous) to the amino terminus of the IL-1Ra mature peptide and the amino terminus of the linker is attached to the carboxy terminus of said amino acid sequence derived from IL-1beta propeptide, wherein the linker comprises at least one amino acid. In another embodiment, said linker comprises an amino acid pair of Lys-Leu.

In another embodiment, the present invention provides a composition comprising the protein of the invention and a carrier. In some embodiment, said composition is a pharmaceutical composition.

In another embodiment, the present invention further provides a polynucleotide comprising a coding portion encoding a protein comprising an amino acid sequence derived from IL-1beta propeptide and an IL-1Ra mature peptide, said amino acid sequence derived from IL-1beta propeptide comprises at least one protease cleavage site. In another embodiment, the present invention further provides an expression vector comprising the polynucleotide as described herein. In another embodiment, the present invention further provides a cell comprising the expression vector as described herein.

In another embodiment, the present invention further provides a method for inhibiting or reducing inflammation in a subject in need thereof, comprising the step of administering to the subject a therapeutically effective amount of the pharmaceutical composition of the invention, thereby inhibiting or reducing inflammation in a subject in need thereof. In another embodiment, the protein exerts its activity only in sites of inflammation and is refractory within a non-inflamed tissue.

In another embodiment, the present invention further provides a method of inhibiting or reducing the binding of IL-1Ra to IL-1R1 in a cell, comprising the step of contacting the cell with a composition of the invention, thereby inhibiting or reducing the binding of IL-1Ra to IL-1R1 in a cell.

In another embodiment, the present invention further provides a method of inhibiting or reducing the binding of IL-1Ra to IL-1R1 in a cell, comprising the step of transfecting the cell with a composition comprising a vector or the polynucleotide as described herein, thereby inhibiting or reducing the binding of IL-1Ra to IL-1R1 in a cell.

In another embodiment, there is provided use of the peptide or composition of the invention for the preparation of medicament for inhibiting or reducing inflammation in a subject in need thereof. In another embodiment, there is provided the peptide or composition of the invention for use in inhibiting or reducing inflammation in a subject in need thereof.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A-F. Expression of NTP-IL-1b upstream to IL-1Ra inhibits its IL-1 receptor antagonizing activity. (1A) A schematic illustration of the Cloning map of IL-1 N-terminal—IL-1Ra chimeric DNA construct. Vector (5,428 bp) and insert (825 bp) are depicted. Restriction enzyme sites for insert and for chimeric link are also indicated. (1B) Diagram of the chimeric-IL-1Ra assembly compared to IL-1Ra alone. (1C) DNA and protein sequence of IL-1beta propeptide N-terminal—IL-1Ra chimeric product. The sequence contains both DNA codons and translated sites of the chimeric molecule. The arrows indicate the border between IL-1beta propeptide—HindIII linker—mature IL-Ra. Furthermore, proteolysis sites are marked by a solid line. (1D) A close-up on the IL-1beta propeptide—HindIII linker—mature IL-Ra junction showing the protease cleavage sites inside the N-terminal region of IL-1beta. Arrows represent established target cleavage sites for (1) elastase, (2) Staph. protease, (3) cathepsin G, elastase, chymase and chymotrypsin, (4) proteinase-3, (5) caspase-1 and (6) granzyme A. (1E) IL-1Ra (left panel) and chimeric-IL-1Ra (right panel)-expressing BL21(DE3) bacterial cells were lysed by sonication and proteins were purified by affinity chromatography. Total cell lysate (TCL) and the purified (Puri.) samples of the above were separated and analyzed on PAGE. (1F) A549 cells were incubated with recombinant chimeric-IL-1Ra, IL-1Ra or Anakinra (concentrations range from 0.78 ng/ml to 50 ng/ml) for 1 h, followed by 6 h stimulation with IL-1b (0.1 ng/ml). The supernatants were collected and IL-6 levels were measured by ELISA (mean±SD, n=3).

FIGS. 7A-D. Lysates of HEK-T293 cells transfected with IL-1Ra or Chimeric IL-1Ra encoding vectors were analyzed by Western blot (7A), showing additional band in the chimeric-IL-1Ra lysate (29.5 kDa) (7B) PAGE analysis of purified recombinant chimeric-IL-1Ra that lacks residues 1-70 of IL-1b (chimeric-IL-1Ra$^{\Delta 1-70}$). (7C) IL-6 levels of A549 cells incubated for 1 h with chimeric-IL-1Ra, chimeric-IL-1Ra$^{\Delta 1-70}$ or Anakinra, followed by 6 h of IL-1b stimulation (0.1 ng/ml). (7D) Chimeric-IL-1Ra$^{\Delta 1-70}$ was digested with elastase (40 µg/ml, 37° C. for 10 min) and analyzed by anti-IL-1Ra Western blot. Anakinra was used as control.

DETAILED DESCRIPTION OF THE INVENTION

Figure 1A:
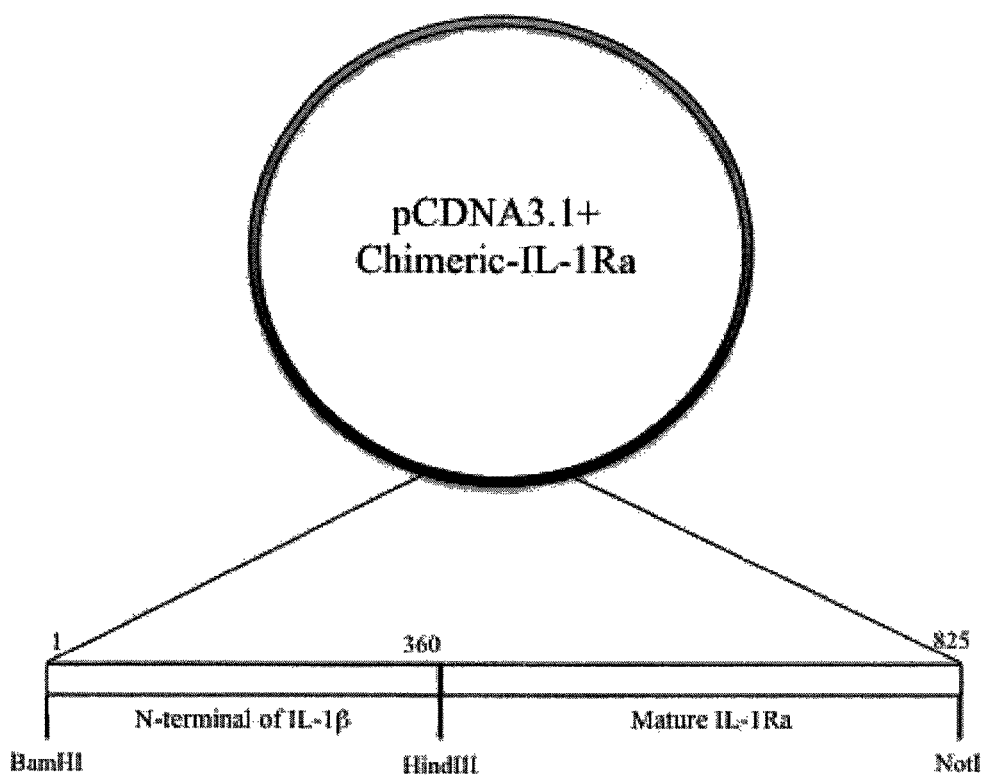

The present invention provides, in some embodiments, chimeric polypeptides comprising IL-1Ra and the N-terminal peptide (NTP) of IL-1β or a fragment thereof, compositions comprising same and methods of use thereof, including but not limited to treatment of an inflammatory disease or disorder.

The present invention is based, in part, on the demonstration that addition of the 1β NTP or fragments thereof, to IL-1Ra, results in an inactive IL-1Ra. By virtue of serine protease cleavage sites contained within IL-1β NTP, inflammation causes cleavage of the chimeric-IL-1Ra, liberating an active form of IL-1Ra. Following its cleavage by enzymes, the chimeric-IL-1Ra was shown to reduce inflammation by blocking IL-1, both in vitro and in vivo. This new approach allows increased safety of anti-IL-1 treatment, and allows extending the use for anti-IL-1 therapy in patients, which prior to the present invention, had increased risk of recurrences of infections and were abstained from anti-IL-1 treatment.

As demonstrated herein below, the chimeric-IL-1Ra cannot antagonize IL-1 in its basic form (i.e., when linked to IL-1Ra NTP or fragment thereof). Increasing doses of the chimeric-IL-1Ra to A549 cells before stimulation with the lowest doses of IL-1β (0.1 ng/ml) did not provide any reduction in IL-6 levels. However, increasing doses of elastase (a protease) enabled the effect of IL-1 antagonizing. Without wishing to be bound by any theory or mechanism of action, this indicates that whenever the chimeric-IL-1Ra reaches inflammation, where proteases are abundant, it is cleaved into an active form, in accordance to the strength of the inflammatory process. In some embodiments, the chimeric peptide described herein is activated by a feedback from the inflammation itself, preventing the need to terminate the treatment due to over-inhibition effect (such as in treatment regimens of Anakinra or anti-IL-1 antibodies). In some embodiments, as long as the site is inflammatory, the chimeric-IL-1Ra will turn active, whereas whenever the inflammatory process is diminished, no proteases are free to cleave the chimeric-IL-1Ra. In some embodiments, the proteolytic process might be inhibited when desired by using the FDA approved α1AT, a well-characterized serine protease inhibitor.

The present invention is further based, in part, on the finding that not only neutrophils, but also macrophages are able to activate the chimeric-IL-1Ra described herein. Macrophages are a key producer of IL-1β. As such these cells secrete the cytokine together with its protease, caspase-1, to the environment. Caspase-1 cleavage site (YVHD; SEQ ID NO: 24) is located at the IL-1β NTP and thus can liberate the IL-1Ra from the interfering N-terminal part. As exemplified herein below, the chimeric-IL-1Ra is activated in vivo. While addition of Anakinra to LPS-containing Matrigel plugs lowered the number of infiltrating cell 24 h following the injection, the chimeric-IL-1Ra was not effective at that point. The short-lived neutrophils die at the site and many proteases are released to the inflammatory site, resulting in activation of the chimeric-IL-1Ra, which was able to reduce inflammation in the next 24 h. This demonstrates that the molecule is able to inhibit inflammation in vivo, and its activity requires an ongoing inflammatory process.

In one embodiment, the present invention provides a protein comprising an amino acid sequence derived from IL-1beta propeptide and an IL-1Ra mature peptide or analogs thereof, wherein the amino acid sequence derived from IL-1beta propeptide comprises at least one protease cleavage site. In another embodiment, said at least one protease cleavage site is a fragment of PIFFDTWDNEAYVHDAPVR (SEQ ID NO: 13). In another embodiment, the at least one protease cleavage site is a serine protease cleavage site. In another embodiment, the at least one protease cleavage site is a caspase cleavage site. In another embodiment, said caspase cleavage site is YVHD (SEQ ID NO: 24).

In another embodiment, the present invention provides a protein comprising at least 20, at least 25, at least 30, at least 35, at least 40, at least 45, at least 50, at least 55, at least 60, at least 65, at least 70, at least 75, at least 80, at least 90, at least 95, at least 100, at least 105, at least 110, at least 115, at least 120 contiguous amino acid residues of IL-1beta propeptide and the IL-1Ra mature peptide. In another embodiment, said contiguous amino acid residues of IL-1beta propeptide comprise at least one protease cleavage site. In another embodiment, said contiguous amino acid residues of IL-1beta propeptide comprise SEQ ID NO: 13.

In another embodiment, the present invention provides a protein that comprises a portion of IL-1beta propeptide's amino terminal and the IL-1Ra mature peptide. In another embodiment, said portion of IL-1beta propeptide comprises or consists of at least amino acid residues 100-120 of IL-1beta propeptide. In another embodiment, said portion of IL-1beta propeptide comprises or consists of at least amino acid residues 95-120 of IL-1beta propeptide. In another embodiment, said portion of IL-1beta propeptide comprises or consists of at least amino acid residues 90-120 of IL-1beta propeptide. In another embodiment, said portion of IL-1beta propeptide comprises or consists of at least amino acid residues 85-120 of IL-1beta propeptide. In another embodiment, said portion of IL-1beta propeptide comprises or consists of at least amino acid residues 80-120 of IL-1beta propeptide. In another embodiment, said portion of IL-1beta propeptide comprises or consists of at least amino acid residues 85-120 of IL-1beta propeptide. In another embodiment, said portion of IL-1beta propeptide comprises or consists of at least amino acid residues 80-120 of IL-1beta propeptide. In another embodiment, said portion of IL-1beta propeptide comprises or consists of at least amino acid residues 75-120 of IL-1beta propeptide. In another embodiment, said portion of IL-1beta propeptide comprises or consists of at least amino acid residues 70-120 of IL-1beta propeptide.

In another embodiment, the phrase "contiguous amino acid residues of IL-1beta propeptide" is of the amino terminal of IL-1beta propeptide (also described herein as IL-1beta's "NTP").

In another embodiment, the protein as described herein further comprises a linker made of at least one amino acid and linking the IL-1beta propeptide portion and the IL-1Ra mature peptide. In another embodiment, the linker is a covalent bond. In another embodiment, the linker is a peptide bond. In another embodiment, the linker is a substituted peptide bond.

In another embodiment, the protein comprises a segment of the IL-1beta propeptide as described herein, a linker, and the IL-1Ra mature peptide, wherein the carboxy terminus of the linker is attached (i.e., contiguous) to the amino terminus of IL-1Ra mature peptide and the amino terminus of the linker is attached to the carboxy terminus of a segment of the IL-1beta propeptide, wherein the linker comprises at least one amino acid. In another embodiment, the linker of the invention comprises or consists of an amino acid pair of Lys-Leu.

In another embodiment, the protein comprises said portion of IL-1beta propeptide, a linker, and the coding sequence of IL-1Ra mature peptide, wherein the carboxy terminus of the linker is attached to the amino terminus of IL-1Ra mature peptide and the amino terminus of the linker is attached to the carboxy terminus of the portion of IL-1beta propeptide, wherein the linker comprises at least one amino acid.

In another embodiment, IL-1beta is Interleukin-1 beta (IL-1) also known as catabolin. In another embodiment, IL-1beta is a cytokine protein that in humans is encoded by the IL1B gene. In another embodiment, IL-1beta comprises the amino acid sequence: APVRSLNCTLRDSQQK-SLVMSGPYELKALHLQGQDMEQQVVFSMSFVQ-GEESNDKIPVA LGLKEKNLYLSCVLKDDKPTLQLES-VDPKNYPKKKMEKRFVFNKIEINNKLEFESAQFPN WYISTSQAENMPVFLGGTKGGQDITDFTMQFVSS (SEQ ID NO: 7). In another embodiment, IL-1beta propeptide comprises the amino acid sequence: MAEVPELASEM-MAYYSGNED DLFFEADGPKQMKCSFQDLDLC-PLDGGIQLRISDHHYSKGFRQAASVVVAMDKLRKML VPCPQTFQENDLSTFFPFIFEEEPIFFDTWDNEAYVH-DAPVRSLNCTLRDSQQKSLVMSGP YELKAL-HLQGQDMEQQVVFSMSFVQGEESNDKIPVAL-GLKEKNLYLSCVLKDDKPTLQ LESVDPKNYPKKKMEKRFVFNKIEINNKLEFESAQF-PNWYISTSQAENMPVFLGGTKGGQ DITDFTMQFVSS (SEQ ID NO: 8).

In another embodiment, the sequence of amino acid residues 1 to 120 of IL-1beta propeptide is:

(SEQ ID NO: 1)
MAEVPELASEMMAYYSGNEDDLFFEADGPKQMKCSFQDLDLCPLDGGIQL

RISDHHYSKGFRQAASVVVAMDKLRKMLVPCPQTFQENDLSTFFPFIFEE

EPIFFDTWDNEAYVHDAPVR.

In another embodiment, the sequence derived from IL-1beta propeptide comprises the amino acid sequence:

(SEQ ID NO: 9)
MDKLRKMLVPCPQTFQENDLSTFFPFIFEEEPIFFDTWDNEAYVHDAPV

R.

In another embodiment, the sequence of IL-1Ra mature peptide comprises or consists the amino acid sequence:

(SEQ ID NO: 2)
RPSGRKSSKMQAFRIWDVNQKTFYLRNNQLVAGYLQGPNVNLEEKIDVVP

IEPHALFLGIHGGKMCLSCVKSGDETRLQLEAVNITDLSENRKQDKRFAF

IRSDSGPTTSFESAACPGWFLCTAMEADQPVSLTNMPDEGVMVTKFYFQE

DE.

In another embodiment, the sequence of the protein of the invention comprises SEQ ID NO: 1 and SEQ ID NO: 2. In another embodiment, the sequence of the protein of the invention comprises SEQ ID NO: 9 and SEQ ID NO: 2. In another embodiment, the sequence of the protein of the invention comprises or consists the amino acid sequence: MAEVPELASEMMAYYSGNEDDLFFEADGPKQM-KCSFQDLDLCPLDGGIQLRISDHH YSKGFRQAASV-VVAMDKLRKMLVPCPQTFQENDLSTFFPFIFEEEP-IFFDTWDNEAYV HDAPVRKLRPSGRKSSKMQAFRIWDVNQKTFYLRN-NQLVAGYLQGPNVNLEEKIDVVPI EPHALFLGIHGG-KMCLSCVKSGDETRLQLEAVNITDLSENRKQDKRFA-FIRSDSGPTTSFE SAACPGWFLCTAMEADQPVSLTNMPDEGVMVTKFY-FQEDE (SEQ ID NO: 3). In another embodiment, the sequence of the protein of the invention comprises or consists the amino acid sequence: MDKLRKMLVPCPQT-FQENDLSTFFPFIFEEEPIFFDTWDNEAYVH-DAPVRKLRP SGRKSSKMQAFRIWDVNQKTFYLRN-NQLVAGYLQGPNVNLEEKIDVVPIEPHALFLGIH GGKMCLSCVKSGDETRLQLEAVNITDLSENRKQD-KRFAFIRSDSGPTTSFESAACPGWFL CTAMEADQPVSLTNMPDEGVMVTKFYFQEDE (SEQ ID NO: 10).

In another embodiment, provided herein a polynucleotide comprising a coding portion encoding a protein as described hereinabove. In another embodiment, provided herein a polynucleotide comprising a coding portion encoding a protein wherein the protein comprises a sequence derived from IL-1beta propeptide and an IL-1Ra mature peptide. In another embodiment, provided herein a polynucleotide comprising a coding portion encoding a protein wherein the protein further comprises a linker, wherein the carboxy terminus of the linker is attached to the amino terminus of IL-1Ra mature peptide and the amino terminus of the linker is attached to the carboxy terminus of the IL-1beta segment.

In another embodiment, the polynucleotide is DNA enloding the amino acid sequence of SEQ ID NO: 3 or SEQ ID NO: 10. In another embodiment, the DNA sequence of residues 1 to 120 of IL-1beta propeptide is:

(SEQ ID NO: 4)
ATGGCAGAAGTACCTGAGCTCGCCAGTGAAATGATGGCTTATTACAGTGG

CAATGAGGATGACTTGTTCTTTGAAGCTGATGGCCCTAAACAGATGAAGT

GCTCCTTCCAGGACCTGGACCTCTGCCCTCTGGATGGCGGCATCCAGCTA

CGAATCTCCGACCACCACTACAGCAAGGGCTTCAGGCAGGCCGCGTCAGT

TGTTGTGGCCATGGACAAGCTGAGGAAGATGCTGGTTCCCTGCCCACAGA

CCTTCCAGGAGAATGACCTGAGCACCTTCTTTCCCTTCATCTTTGAAGAA

GAACCTATCTTCTTCGACACATGGGATAACGAGGCTTATGTGCACGATGC

ACCTGTACGA.

In another embodiment, the DNA sequence of IL-1Ra mature peptide comprises or consists the sequence:

(SEQ ID NO: 5)
CGACCCTCTGGGAGAAAATCCAGCAAGATGCAAGCCTTCAGAATCTGGGA

TGTTAACCAGAAGACCTTCTATCTGAGGAACAACCAACTAGTTGCTGGAT

ACTTGCAAGGACCAAATGTCAATTTAGAAGAAAAGATAGATGTGGTACCC

ATTGAGCCTCATGCTCTGTTCTTGGGAATCCATGGAGGGAAGATGTGCCT

GTCCTGTGTCAAGTCTGGTGATGAGACCAGACTCCAGCTGGAGGCAGTTA

ACATCACTGACCTGAGCGAGAACAGAAAGCAGGACAAGCGCTTCGCCTTC

ATCCGCTCAGACAGTGGCCCCACCACCAGTTTTGAGTCTGCCGCCTGCCC

CGGTTGGTTCCTCTGCACAGCGATGGAAGCTGACCAGCCCGTCAGCCTCA

CCAATATGCCTGACGAAGGCGTCATGGTCACCAAATTCTACTTCCAGGAG

GACGAGTAG.

In another embodiment, the DNA sequence of the protein of the invention comprises or consists the sequence:

(SEQ ID NO: 6)
ATGGCAGAAGTACCTGAGCTCGCCAGTGAAATGATGGCTTATTACAGTGG

CAATGAGGATGACTTGTTCTTTGAAGCTGATGGCCCTAAACAGATGAAGT

GCTCCTTCCAGGACCTGGACCTCTGCCCTCTGGATGGCGGCATCCAGCTA

CGAATCTCCGACCACCACTACAGCAAGGGCTTCAGGCAGGCCGCGTCAGT

```
-continued
TGTTGTGGCCATGGACAAGCTGAGGAAGATGCTGGTTCCCTGCCCACAGA

CCTTCCAGGAGAATGACCTGAGCACCTTCTTTCCCTTCATCTTTGAAGAA

GAACCTATCTTCTTCGACACATGGGATAACGAGGCTTATGTGCACGATGC

ACCTGTACGAAAGCTTCGACCCTCTGGGAGAAAATCCAGCAAGATGCAAG

CCTTCAGAATCTGGGATGTTAACCAGAAGACCTTCTATCTGAGGAACAAC

CAACTAGTTGCTGGATACTTGCAAGGACCAAATGTCAATTTAGAAGAAAA

GATAGATGTGGTACCCATTGAGCCTCATGCTCTGTTCTTGGGAATCCATG

GAGGGAAGATGTGCCTGTCCTGTGTCAAGTCTGGTGATGAGACCAGACTC

CAGCTGGAGGCAGTTAACATCACTGACCTGAGCGAGAACAGAAAGCAGGA

CAAGCGCTTCGCCTTCATCCGCTCAGACAGTGGCCCCACCACCAGTTTTG

AGTCTGCCGCCTGCCCCGGTTGGTTCCTCTGCACAGCGATGGAAGCTGAC

CAGCCCGTCAGCCTCACCAATATGCCTGACGAAGGCGTCATGGTCACCAA

ATTCTACTTCCAGGAGGACGAGTAG.
```

In another embodiment, the DNA sequence of the protein of the invention comprises or consists of the sequence: (SEQ ID NO: 12).

In another embodiment, the invention further provides an expression vector comprising a polynucleotide of the invention. In another embodiment, the invention further provides a cell comprising the expression vector of the invention. In another embodiment, a composition of the invention comprises the expression vector of the invention and/or a polynucleotide of the invention a polynucleotide of the invention and/or a cell comprising the expression vector and a suitable carrier.

In some embodiments, the terms "polypeptide" or "protein" as used herein encompasses native polypeptides or peptides (either degradation products, synthetically synthesized polypeptides, proteins, chimeras or recombinant polypeptides) and peptidomimetics (typically, synthetically synthesized proteins), as well as peptoids and semipeptoids which are protein analogs, which have, in some embodiments, modifications rendering the protein of the invention more stable while in a body or more capable of penetrating into tissues and cells.

In some embodiments, modifications include, but are not limited to N terminus modification, C terminus modification, polypeptide or peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, peptide bonds (—CO—NH—) within the protein of the invention are substituted. In some embodiments, the peptide bonds are substituted by N-methylated bonds (—N(CH3)-CO—). In some embodiments, the peptide bonds are substituted by ester bonds (—C(R)H—C—O—O—C(R)—N—). In some embodiments, the peptide bonds are substituted by ketomethylen bonds (—CO—CH2-). In some embodiments, the peptide bonds are substituted by α-aza bonds (—NH—N(R)—CO—), wherein R is any alkyl, e.g., methyl, carba bonds (—CH2-NH—).

In some embodiments, the peptide bonds are substituted by hydroxyethylene bonds (—CH(OH)—CH2-). In some embodiments, the peptide bonds are substituted by thioamide bonds (—CS—NH—). In some embodiments, the peptide bonds are substituted by olefinic double bonds (—CH=CH—). In some embodiments, the peptide bonds are substituted by retro amide bonds (—NH—CO—). In some embodiments, the peptide bonds are substituted by peptide derivatives (—N(R)—CH2-CO—), wherein R is the "normal" side chain, naturally presented on the carbon atom. In some embodiments, these modifications occur at any of the bonds along the peptide chain and even at several (2-3 bonds) at the same time.

In some embodiments, natural aromatic amino acids of the protein of the invention such as Trp, Tyr and Phe, be substituted for synthetic non-natural acid such as Phenylglycine, TIC, naphthylelanine (Nol), ring-methylated derivatives of Phe, halogenated derivatives of Phe or o-methyl-Tyr. In some embodiments, the protein of the invention include one or more modified amino acid or one or more non-amino acid monomers (e.g. fatty acid, complex carbohydrates etc).

In one embodiment, "amino acid" or "amino acid" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the protein of the invention are utilized in therapeutics which requires the protein of the invention to be in a soluble form. In some embodiments, the protein of the invention include one or more non-natural or natural polar amino acid, including but not limited to serine and threonine which are capable of increasing protein solubility due to their hydroxyl-containing side chain.

In some embodiments, the protein of the invention are utilized in a linear form, although it will be appreciated by one skilled in the art that in cases where cyclicization does not severely interfere with protein characteristics, cyclic forms of the protein can also be utilized.

In some embodiments, the protein of the invention is biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the protein is relatively short (about 5-15 kDa) and/or when it cannot be produced by recombinant techniques (i.e., not encoded by a nucleic acid sequence) and therefore involves different chemistry.

In some embodiments, solid phase peptide synthesis procedures are well known to one skilled in the art and further described by John Morrow Stewart and Janis Dillaha Young, Solid Phase protein Syntheses (2nd Ed., Pierce Chemical Company, 1984). In some embodiments, synthetic proteins are purified by preparative high performance liquid chromatography [Creighton T. (1983) Proteins, structures and molecular principles. WH Freeman and Co. N.Y.] and the composition of which can be confirmed via amino acid sequencing by methods known to one skilled in the art.

In some embodiments, recombinant protein techniques are used to generate the protein of the invention. In some embodiments, recombinant protein techniques are used for generation of relatively long peptides (e.g., longer than 18-25 amino acid). In some embodiments, recombinant protein techniques are used for the generation of large amounts of the protein of the invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al, (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In one embodiment, a protein of the invention is synthesized using a polynucleotide encoding a protein of the invention. In some embodiments, the polynucleotide encoding the protein of the invention is ligated into an expression vector, comprising a transcriptional control of a cis-regulatory sequence (e.g., promoter sequence). In some embodiments, the cis-regulatory sequence is suitable for directing constitutive expression of the protein of the invention. In some embodiments, the cis-regulatory sequence is suitable for directing tissue specific expression of the protein of the invention. In some embodiments, the cis-regulatory sequence is suitable for directing inducible expression the protein of the invention.

In some embodiment, tissue-specific promoters suitable for use with the present invention include sequences which are functional in specific cell population, example include, but are not limited to promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). Inducible promoters suitable for use with the present invention include for example the tetracycline-inducible promoter (Srour, M. A., et al., 2003. Thromb. Haemost. 90: 398-405).

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase.

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the protein of the invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide for the secretion of the protein of the invention. In some embodiments, signal sequences include, but are not limited to the endogenous signal sequences Each possibility represents a separate embodiment of the present invention.

In one embodiment, following expression and secretion, the signal peptides are cleaved from the precursor proteins resulting in the mature proteins. In another embodiment, the term "protein" as used herein encompasses a "chimera protein".

In some embodiments, polynucleotides of the present invention are prepared using PCR techniques, or any other method or procedure known to one skilled in the art. In some embodiments, the procedure involves the legation of two different DNA sequences (See, for example, "Current Protocols in Molecular Biology", eds. Ausubel et al., John Wiley & Sons, 1992).

In one embodiment, proteins of the present invention are inserted into expression vectors (i.e., a nucleic acid construct) to enable expression of the recombinant protein. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhances) and transcription and translation terminators (e.g., polyadenylation signals).

In one embodiment, a variety of prokaryotic or eukaryotic cells can be used as host-expression systems to express the proteins of the present invention. In some embodiments, these include, but are not limited to, microorganisms, such as bacteria transformed with a recombinant bacteriophage DNA, plasmid DNA or cosmid DNA expression vector containing the protein coding sequence; yeast transformed with recombinant yeast expression vectors containing the protein coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the protein coding sequence.

In some embodiments, non-bacterial expression systems are used (e.g. mammalian expression systems such as CHO cells) to express the protein of the present invention. In one embodiment, the expression vector used to express polynucleotides of the present invention in mammalian cells is pCI-DHFR vector comprising a CMV promoter and a neomycin resistance gene. Construction of the pCI-dhfr vector is described, according to one embodiment, in Example 1.

In some embodiments, in bacterial systems of the present invention, a number of expression vectors can be advantageously selected depending upon the use intended for the protein expressed. In one embodiment, large quantities of protein are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the protein. In one embodiment, vectors adaptable to such manipulation include, but are not limited to, the pET series of E. coli expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric protein.

In some embodiments, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A⁺, pMTO10/A⁺, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors are useful for in vivo expression of the proteins of the present invention since they offer advantages such as lateral infection and targeting specificity. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the proteins of the present invention can also be expressed from a nucleic acid construct administered to the individual employing any suitable mode of administration, described hereinabove (i.e., in-vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

In one embodiment, in vivo gene therapy using EPO has been attempted in animal models such as rodents [Bohl et al., Blood. 2000; 95:2793-2798], primates [Gao et al., Blood, 2004, Volume 103, Number 9] and has proven successful in human clinical trials for patients with chronic renal failure [Lippin et al Blood 2005, 106, Number 7].

In one embodiment, plant expression vectors are used. In one embodiment, the expression of a protein coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the protein), the expression construct of the present invention can also include sequences engineered to optimize stability, production, purification, yield or activity of the expressed protein.

Various methods, in some embodiments, can be used to introduce the expression vector of the present invention into the host cell system. In some embodiments, such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6):

504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, transformed cells are cultured under effective conditions, which allow for the expression of high amounts of recombinant protein. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant protein of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant proteins of the present invention either remain within the recombinant cell, secreted into the fermentation medium, secreted into a space between two cellular membranes, such as the periplasmic space in *E. coli*; or retained on the outer surface of a cell or viral membrane.

In one embodiment, following a predetermined time in culture, recovery of the recombinant protein is affected.

In one embodiment, the phrase "recovering the recombinant/chimera protein" used herein refers to collecting the whole fermentation medium containing the protein and need not imply additional steps of separation or purification.

In one embodiment, proteins of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the protein of the present invention and fused cleavable moiety. In one embodiment, a fusion protein can be designed so that the protein can be readily isolated by affinity chromatography; e.g., by immobilization on a column specific for the cleavable moiety. In one embodiment, a cleavage site is engineered between the protein and the cleavable moiety and the protein can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the protein of the present invention is retrieved in "substantially pure" form.

In one embodiment, the phrase "substantially pure" refers to a purity that allows for the effective use of the protein in the applications described herein.

In one embodiment, the protein of the present invention can also be synthesized using in vitro expression systems. In one embodiment, in vitro synthesis methods are well known in the art and the components of the system are commercially available.

Pharmaceutical Use

In another embodiment, the present invention further provides a method for inhibiting or reducing inflammation in a subject in need thereof, comprising the step of administering to the subject a composition comprising an effective amount of a protein of the invention, thereby inhibiting or reducing inflammation in a subject in need thereof. In another embodiment, the present invention further provides a method for inhibiting or reducing inflammation in a subject in need thereof, comprising the step of administering to the subject a composition comprising an effective amount of a polynucleotide/vector of the invention, thereby inhibiting or reducing inflammation in a subject in need thereof. In another embodiment, the present invention provides methods of inhibiting or reducing the binding of IL-1Ra to IL-1R1 in a cell. In some embodiments, the invention provides methods for treating IL-1 associated diseases or disorders, including but not limited to type 1 diabetes, type 2 diabetes, gout, cardiac remodeling, rheumatoid arthritis and osteoarthritis.

In another embodiment, inflammation is an infection. In another embodiment, inflammation is a chronic infection such as HIV, inflammatory bowel disease, or septic episodes. In another embodiment, inflammation includes a catabolic illness. In another embodiment, inflammation is Crohn's disease. In another embodiment, inflammation is short bowel syndrome. In another embodiment, inflammation is arthritis. In another embodiment, inflammation is Acne Vulgaris. In another embodiment, inflammation is Alzheimer'S disease. In another embodiment, inflammation is Asthma. In another embodiment, inflammation is Atherosclerosis. In another embodiment, inflammation is an autoimmune disease. In another embodiment, inflammation is Celiac Disease. In another embodiment, inflammation is Prostatitis. In another embodiment, inflammation is Colitis. In another embodiment, inflammation is Dermatitis. In another embodiment, inflammation is Diverticulitis. In another embodiment, inflammation is Glomerulonephritis. In another embodiment, inflammation is Hepatitis. In another embodiment, inflammation is Hypersensitivities. In another embodiment, inflammation is Interstitial Cystitis. In another embodiment, inflammation is Irritable Bowel Syndrome. In another embodiment, inflammation is Lupus Erythematous. In another embodiment, inflammation is Nephritis. In another embodiment, inflammation is Parkinson's disease. In another embodiment, inflammation is Pelvic Inflammatory Disease. In another embodiment, inflammation is a reperfusion injury. In another embodiment, inflammation is Rheumatoid Arthritis. In another embodiment, inflammation is Sarcoidosis. In another embodiment, inflammation is transplant rejection. In another embodiment, inflammation is Ulcerative Colitis. In another embodiment, inflammation is Vasculitis. In another embodiment, inflammation is ankylosing spondylitis.

In another embodiment, "a subject" is a subject in need of a treatment comprising the protein of the invention. In another embodiment, a subject as described herein is a subject suffering from inflammation or susceptible to inflammation such as but not limited to a subject undergoing surgical recovery. In another embodiment, a subject as described herein is a subject undergoing organ transplantation such as liver transplantation. In another embodiment, a subject as described herein is a subject suffering from long term oxidative stress. In another embodiment, a subject as described herein is a subject suffering from low reduced glutathione (GSH) levels. In another embodiment, a subject as described herein is a subject suffering from low vitamin D and other antioxidants. In another embodiment, a subject as described herein is a subject suffering from high oxidised glutathione (GSSG) levels. In another embodiment, a subject as described herein is a subject suffering from high malondialdehyde (a marker for oxidative stress, formed when fats are oxidized). In another embodiment, a subject as described herein is a subject suffering from increased lipid peroxidation. In another embodiment, a subject as described herein is a subject suffering from high homocysteine. In another embodiment, a subject as described herein is a subject suffering from high fructosamine. In another embodiment, a subject as described herein is a subject suffering from high CRP. In another embodiment, a subject as described herein is a subject suffering from isoprostanes (a marker for oxidative stress, formed when fats are oxidized). In another embodiment, a subject as described herein is a subject suffering from an increase in sugar and foods which convert to glucose. In another embodiment, a subject as described herein is a subject suffering from decreased selenium levels, selenium is needed for the production of glutathione. In another embodiment, a subject as described herein is a subject suffering from increased oestrogen levels, oestrogen is an excitatory, inflammatory hormone decreased zinc and increased copper. In another embodiment, a subject as described herein is a subject suffering from a high level of matrix metalloproteinases (MMPs). In another embodiment, a subject as described herein is a subject suffering from a lack of progesterone. In another embodiment, a subject as described herein is a subject suffering from a predominance of the inflammatory Th1 cytokines over the anti-inflammatory Th2 cytokines. In another embodiment, a subject as described herein is a subject suffering from emotional stress. In another embodiment, a subject as described herein is a subject suffering from an allergy. In another embodiment, a subject as described herein is a subject suffering from a high level of advanced glycation endproducts. In another embodiment, a subject as described herein is a subject suffering from environmental pollutants. In another embodiment, a subject as described herein is a subject suffering from a high level of tumour necrosis factor-alpha. In another embodiment, a subject as described herein is a subject suffering from a high level of prolactin. In another embodiment, a subject as described herein is a subject suffering from increased levels of fructosamine. In another embodiment, a subject as described herein is a subject suffering from increased levels of homocysteine. In another embodiment, a subject as described herein is a subject suffering from a high level of pro-inflammatory HDLs. In another embodiment, a subject as described herein is a subject suffering from a deficiency of the essential fatty acid Omega 3. In another embodiment, a subject as described herein is a subject suffering from decreased levels of vitamins B2, C, E and beta-carotene.

In another embodiment, the subject is a mammal. In another embodiment, the subject is a lab animal. In another embodiment, the subject is a pet. In another embodiment, the subject is a rodent. In another embodiment, the subject is a farm animal. In another embodiment, the subject is a human subject. In another embodiment, the subject is a peri-menopausal woman. In another embodiment, the subject is a woman suffering of oestrogen excess.

In another embodiment, the protein exerts its inflammation inhibitory activity only in sites of inflammation. In another embodiment, the protein of the invention is refractory in terms of its anti-inflammatory activity in a non-inflamed tissue. In another embodiment, inhibiting inflammation is specifically targeting inflammatory sites. In another embodiment, inhibiting inflammation is inhibiting an inflammation mediator at a site of inflammation and not at a site of no inflammatory activity.

In another embodiment, the present invention provides methods of IL-1 treatment without putting the treated subject in risk of pathogen (e.g., bacterial) infections or neutropenia. In another embodiment, the protein and methods of the invention are useful for treatment of patients with high risk for infection.

The chimeric-IL-1Ra inflammation-dependent activity is important for the treatment of cancer patients. Chronic inflammation is one of the characters of the tumor microenvironment. It is surrounded with myeloid cells, like neutrophils and macrophages; it is plentiful with enzymes and cytokines. IL-1 has a major role in the carcinogenesis process, and also in the growth and metastases of tumors. It is an important angiogenic factor, and blocking it was demonstrated to be effective in reducing tumor size, angiogenesis and metastases. However, cancer patients might be treated for long periods and to use chemotherapy drugs, which already reduce their WBC count. The present invention provides, in some embodiments, methods of anti-IL-1 therapy (e.g., inhibiting IL-1) without risking the patient with infections and reducing the neutrophil numbers. In another embodiment, the protein and methods of the invention are useful for treatment of subjects having IL-1 producing tumors, including cancer cells directly producing IL-1 or tumor microenvironment producing high IL-1 concentrations.

In another embodiment, the invention further provides a method of inhibiting the binding of IL-1Ra to IL-1R1 in a cell, comprising the step of contacting the cell with a composition comprising an effective amount of a protein of the invention, thereby inhibiting the binding of IL-1Ra to IL-1R1 in a cell.

In another embodiment, provided herein a method of inhibiting the binding of IL-1Ra to IL-1R1 in a cell, comprising the step of transfecting the cell with the composition comprising a polynucleotide and/or a vector as described herein, thereby inhibiting the binding of IL-1Ra to IL-1R1 in a cell.

In another embodiment, the cell is an inflammatory cell. In another embodiment, an inflammatory cell is a cell participating in the inflammatory response to a foreign substance. In another embodiment, an inflammatory cell is a neutrophil. In another embodiment, an inflammatory cell is a macrophage. In another embodiment, an inflammatory cell is a monocytes. In another embodiment, an inflammatory cell is an eosinophil. In another embodiment, an inflammatory cell is a basophil. In another embodiment, an inflammatory cell is a mononucleated cell. In another embodiment, an inflammatory cell is a cell that secrets pro-inflammatory cytokines. In another embodiment, an inflammatory cell is a cell affected by pro-inflammatory cytokines.

In one embodiment, a protein of the present invention can be provided to an individual/subject per se.

Pharmaceutical Compositions

In one embodiment, the protein of the present invention can be provided to the individual as part of a pharmaceutical composition where it is mixed with a pharmaceutically acceptable carrier. In another embodiment, the protein of the present invention can be provided to the individual as part of a pharmaceutical composition where it is mixed with at least one additional anti-inflammatory agent and a pharmaceutically acceptable carrier.

In one embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In one embodiment, "active ingredient" refers to the protein sequence of interest, which is accountable for the biological effect.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In one embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In one embodiment, the preparation is administered in a local rather than systemic manner, for example, via injection of the preparation directly into a specific region of a patient's body.

Various embodiments of dosage ranges are contemplated by this invention. The dosage of the protein of the present invention, in one embodiment, is in the range of 0.05-80 µg/day. In another embodiment, the dosage is in the range of 0.05-50 µg/day. In another embodiment, the dosage is in the range of 0.1-20 µg/day. In another embodiment, the dosage is in the range of 0.1-10 µg/day. In another embodiment, the dosage is in the range of 0.1-5 µg/day. In another embodiment, the dosage is in the range of 0.5-5 µg/day. In another embodiment, the dosage is in the range of 0.5-50 µg/day. In another embodiment, the dosage is in the range of 5-80 µg/day. In another embodiment, the dosage is in the range of 35-65 µg/day. In another embodiment, the dosage is in the range of 35-65 µg/day. In another embodiment, the dosage is in the range of 20-60 µg/day. In another embodiment, the dosage is in the range of 40-60 µg/day. In another embodiment, the dosage is in a range of 45-60 µg/day. In another embodiment, the dosage is in the range of 40-60 µg/day. In another embodiment, the dosage is in a range of 60-120 µg/day. In another embodiment, the dosage is in the range of 120-240 µg/day. In another embodiment, the dosage is in the range of 40-60 µg/day. In another embodiment, the dosage is in a range of 240-400 µg/day. In another embodiment, the dosage is in a range of 45-60 µg/day. In another embodiment, the dosage is in the range of 15-25µ/day. In another embodiment, the dosage is in the range of 5-10 µg/day. In another embodiment, the dosage is in the range of 55-65 µg/day.

In one embodiment, the dosage is 20 µg/day. In another embodiment, the dosage is 30 µg/day. In another embodiment, the dosage is 40 µg/day. In another embodiment, the dosage is 50 µg/day. In another embodiment, the dosage is 60 µg/day. In another embodiment, the dosage is 70 µg/day. In another embodiment, the dosage is 80 µg/day. In another embodiment, the dosage is 90 µg/day. In another embodiment, the dosage is 100 µg/day.

Oral administration, in one embodiment, comprises a unit dosage form comprising tablets, capsules, lozenges, chewable tablets, suspensions, emulsions and the like. Such unit dosage forms comprise a safe and effective amount of the desired compound, or compounds, each of which is in one embodiment, from about 0.7 or 3.5 µg to about 280 µg/70 kg, or in another embodiment, about 0.5 or 10 µg to about 210 µg/70 kg. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.012% to about 0.933% of the desired compound or compounds, or in another embodiment, from about 0.033% to about 0.7%.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In some embodiments, h compositions comprise from about 0.01% to about 10.0% w/v of a subject compound, more preferably from about 0.1% to about 2.0, which is used for systemic delivery of the compounds by the intranasal route.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In another embodiment, the active compound can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. *Biomed. Eng.* 14:201 (1987); Buchwald et al., Surgery 88:507 (1980); Saudek et al., *N. Engl. J. Med.* 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in *Medical Applications of Controlled Release*, supra, vol. 2, pp. 115-138 (1984). Other controlled release systems are discussed in the review by Langer (*Science* 249:1527-1533 (1990).

In some embodiments, the active ingredient is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

The compositions also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise local anesthetics or other actives. The compositions can be used as sprays, mists, drops, and the like.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In some embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also be prepared, placed in an appropriate container, and labeled for treatment of an indicated condition.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the proteins of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Cloning of Chimeric-IL-1Ra and IL-1Ra Alone

IL-1β propeptide and IL-1Ra were amplified by conventional PCR reaction from human cDNA using the primers described in Table 1. The PCR products of IL-1β propeptide and IL-1Ra were digested with HindIII (NEB) in order to create adhesive linker between the two molecules and were ligated using T4 ligase. The digested molecules were ligated, and were further digested with BamHI and NotI (both purchased from NEB). The ligated chimera (IL-1β propeptide-IL-1Ra chimera) or IL-1Ra alone products were cloned into pCDNA3.1+ plasmid (Invitrogen). In order to create a deletion mutations of IL-1β NTP in the chimeric-IL-1Ra, 5'-phosphorylated primers f and g flanking codons encoding residues 102-120, or for residues 1-70, 5'-phosphorylated primers h and i were used. The template used was 100 pg pCDNA3.1+ chimeric-IL-1Ra plasmid, amplified by Phusion DNA polymerase (New England Biolabs) in PCR program: initial denaturation 98° C.-30 sec then 25 cycles of 98° C.-10 sec; 65° C.-10 sec; 72° C.-3 min and 30 sec; and final extension of 72° C. for 5 min. Sequences were verified by sequencing analysis from both sides of the inserts using T7 promoter and BGH-Reverse primers. Cloning into pET30a (Novagen) of chimeric-IL-1Ra and Δ102-120 mutated chimeric-IL-1Ra was performed with primers a and d, IL-1Ra alone with primers e and d, while Δ1-70 mutated chimeric-IL-1Ra coding sequence was amplified using primer j and d. Using BamHI and NotI sites, the products were cloned into pET30a in frame with the N-terminal His tag. Sequences were verified by sequencing analysis at both sides of the inserts using T7 and BGH primers.

TABLE 1

Primers used in cloning

| Primer | Sequence | SEQ ID NO: |
|---|---|---|
| a | CACGGATCCGCCACCATGGCAGAAGTACCTGAGCTC | 14 |
| b | CACAAGCTTTCGTACAGGTGCATCGTGCACATAAG | 15 |
| c | CACAAGCTTCGACCCTCTGGGAGAAAATCCAG | 16 |
| d | TCACAGTGCGGCCGCCTACTCGTCCTCCTGGAAGTAG | 17 |
| e | CAGGATCCGCCACCATGCGACCCTCTGGGAGAAAATCCAG | 18 |
| f | Phospho 5' - CGA CCC TCT GGG AGA AAA TCC A | 19 |
| g | Phospho 5' - TTC TTC TTC AAA GAT GAA GGG AAA GAA GGT | 20 |
| h | Phospho 5' - ATG GAC AAG CTG AGG AAG ATG CTG | 21 |

TABLE 1-continued

Primers used in cloning

| Primer | Sequence | SEQ ID NO: |
|---|---|---|
| i | Phospho 5' - GCA GAT CGT CTC TGA ATG GAA CAG G | 22 |
| j | CAC GGA TCC ATG GAC AAG AAG CTG AGG AAG ATG CTG | 23 |

Restriction sites within the primers of table 1: GGATCC-BamHI; GCCACC-Kozak; AAGCTT-HindIII; GCGGCCGC-NotI; and CTA-stop codon.

Recombinant Protein Preparation

BL21(DE3) bacterial cells were transformed with pET30a cloned vectors and were grown in LB supplemented with Kanamycin (30 µg/ml). Bacterial cells were grown to logarithmic phase, and were induced with 0.1 mM IPTG for 2 h, then centrifuged and re-suspended in 10 mM imidazole followed by sonication (4 times, 20 sec with 40% amplitude). Recombinant proteins were isolated using affinity chromatography with Ni-NTA agarose beads according to the manufacturer protocol (Thermo Scientific). Imidazole eluted fractions (250 mM) were desalted with sterile DDW using 10 kDa Amicon Ultra centrifugal filters (Millipore). In order to cut the His tag and linker originated from pET30a vector from the N-terminal of the chimeric-IL-1Ra, chimeric-IL-1Ra$^{\Delta 102-120}$, chimeric-IL-1Ra$^{\Delta 1-70}$ or IL-1Ra alone, recombinant enterokinase (Novagen) digestion was performed (20° C. for 20 h), following with enterokinase removal capture beads purification step (Novagen).

Transfections of HEK-T293 Cells and Lysates Preparation

HEK-T293 cells were cultured in 10 cm culture dishes, and the following day were transfected with 8 µg of either pCDNA3.1+ empty vector, IL-1Ra or the chimera encoding vector with JetPEI transfection reagent (Polyplus Transfection). After 24 h cells were washed twice in PBS, harvested, centrifuged and lysates were prepared using 0.5% triton-X100 in PBS. Lysates were then dialyzed against RPMI medium using 3,500 molecular weight cut-off dialysis bags (Spectrum Laboratories). RAW264.7 were cultured in 10% FCS supplemented RPMI, and were stimulated with 1 µg/ml LPS (Sigma) for 20 h, with or without 5 mM ATP for 30 min.

Western Blot and ELISA

Lysates of transfected HEK-T293 cells or recombinant chimeric-IL-1Ra, chimeric-IL-1Ra$^{\Delta 102-120}$, chimeric-IL-1Ra$^{\Delta 1-70}$ and recombinant IL-1Ra proteins were analyzed for protein concentration by Bradford reagent (Bio-Rad), boiled in 95° C. dry bath together with Laemmli sample buffer, and equal amounts were separated over polyacrylamide gel-electrophoresis (PAGE), transferred to PVDF membrane followed by western blot using goat anti-IL-1Ra antibody (R&D Systems). Membranes were imaged using Chemidoc XRS imager (Bio-Rad). In order to calculate the chimera's and IL-1Ra's concentrations, lysates were also analyzed by IL-1Ra DuoSet ELISA kit (R&D Systems).

A549 Cells Stimulation with IL-1

A sub-clone of A549 cell line was cultured in 96 well plates (4×10$^4$/well) and on the following day recombinant IL-1Ra (anakinra) or transfected HEK-T293 cell lysates were added to the cell culture media for 1 h followed by 6 h of stimulation with 100 pg/ml recombinant IL-1beta. Culture media of stimulated A549 cells were analyzed for the levels of IL-6 by ELISA kit (PeproTech). Lysates were also digested before addition to A549 cells by 40 µg/ml neutrophil elastase (Athens Research & Technology) in 37° C. for 10 min then were either added to A549 cell medium for testing IL-1R1 inhibition (7.5 µg total lysate of chimeric-IL-1Ra or mock transfected cell lysates) or were heated in 95° C. dry bath together with Laemmli sample buffer and western blot was conducted as described above.

Enzymatic Assays

Recombinant protein or HEK-T293 cell lysates were digested before addition to A549 cells by 40 µg/ml elastase (Athens Research & Technology) in 37° C. for 10 min then were either added to A549 cell medium for testing IL-1R1 inhibition. In order to inhibit elastase digestion, 0.5 µg/ml α1-AT (Aralast) was added prior to elastase to the reaction tubes. For elastase/chimeric-IL-1Ra dose response assays, serial dilutions of elastase (1:5) or chimeric-IL-1Ra (1:3) were performed, then mixed and incubated for 15 min in 37° C. Later, each enzymatic reaction was added to 4 wells of 96 well plates with A549 cells, and IL-1β inhibition assay was performed (as described). RAW264.7 cell supernatants (50 µl) or lysates (5 µg) were incubated with 500 ng of chimeric-IL-1Ra, and were analyzed by Western blot.

Inflammation in Matrigel Plugs

Matrigel (BD Biosciences) was thawed and mixed with 1 µg LPS with or without 1 µg recombinant chimeric-IL-1Ra or Anakinra, and 500 µl was injected subcutaneously into C57BL/6 mice (Harlan Laboratories). Following 24 h or 48 h Matrigel plugs were removed from mice and dissolved using Collagenase IV (Sigma) for 90 min in 37° C. incubator with magnetic stirrer. The cells were filtered using 70 µM cell strainer (BD Biosciences), washed twice in PBS and were counted with Countess automated cell counter (Invitrogen).

Example 1

Figure 1B:
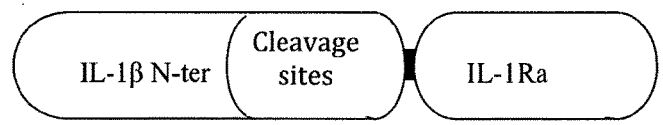
Figure 1D:
Figure 1E:
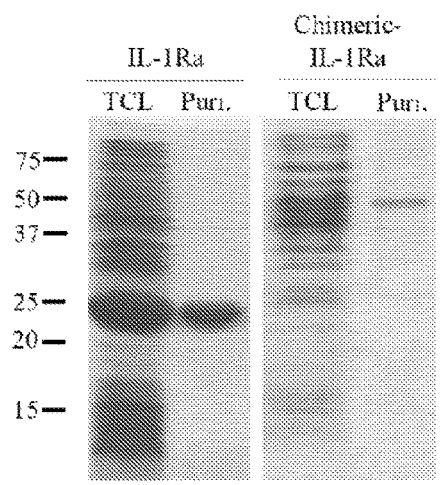

Generation of Chimeric Molecule Combined from IL-1Beta Propeptide and Mature IL-1Ra In order to create one molecule combining the N-terminal propeptide of IL-1beta and the mature IL-1Ra (which lacks the signal peptide), both of the sequences were amplified by PCR from human cells cDNA, ligated and cloned into pCDNA3.1+ plasmid, as illustrated in FIGS. 1A and 1B. IL-1Ra coding sequence was maintained within the reading frame of the IL-1 beta propeptide sequence (FIG. 1C). The section that was chosen to be cloned from IL-1beta, contained residues 1 to 120, since this segment contains in its last 17 residues several target cleavage sites that were demonstrated to activate the precursor of IL-1beta, by cleaving it into the truncated active form during inflammation (FIG. 1D). Chimeric-IL-1Ra sequence, as well as the sequence for IL-1Ra alone, were cloned into a pET30a vector downstream to the His tag and linker sequences. The proteins were expressed in BL21(DE3) bacterial cells and were isolated by Ni-NTA affinity chromatography (FIG. 1E).

Figure 1F:
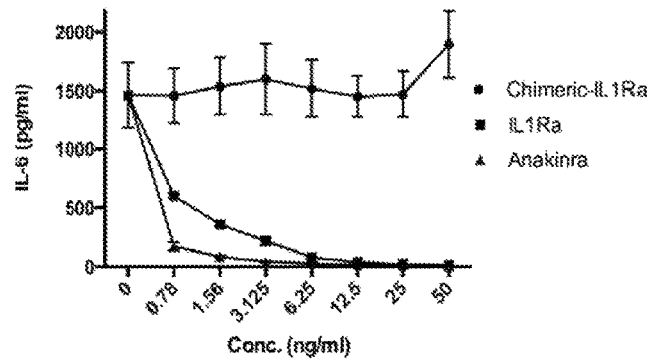
Figure 9A:
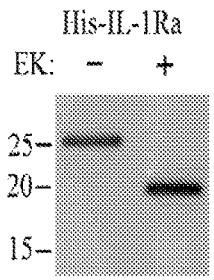
FIGS. 9A-F. The effect of His tag removal from Chimeric-IL-1Ra and IL-1Ra recombinant protei<sup>no</sup>. Western blots using anti-IL-1Ra antibody of His-IL-1Ra (9A); His-chimeric-IL-1Ra (9C) or His-chimeric-IL-1Ra$^{\Delta 1-70}$ (9E) recombinants proteins that were digested with enterokinase (EK; 0.3U, 20° C., 20 h), in order to liberate the desired protein from the His-tag-linker derived from the expression vector (pET30a, Novagen). The effect of EK cleavage on the activity of the recombinant His-IL-1Ra (9B); His-chimeric-IL-1Ra (9D) or His-chimeric-IL-1Ra$^{\Delta 1-70}$ (9F) is demonstrated by IL-1b inhibition experiments, in which A549 cells were incubated with the recombinant purified proteins containing the His tag and the linker, or following EK digestion (concentrations range from 0.78 ng/ml to 50 ng/ml). Alternatively, Anakinra was used. After 1 h, the cells were stimulated with IL-1b (0.1 ng/ml) for 6 h. The supernatants were collected and IL-6 levels were measured by ELISA.
Figure 9B:
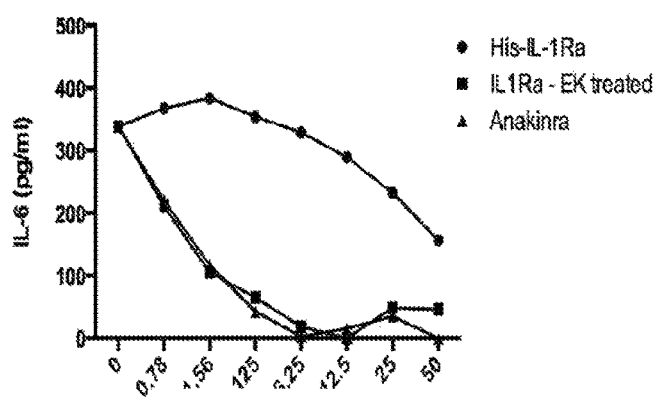
Figure 9C:
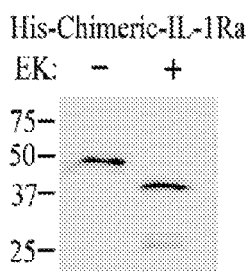
Figure 9D:
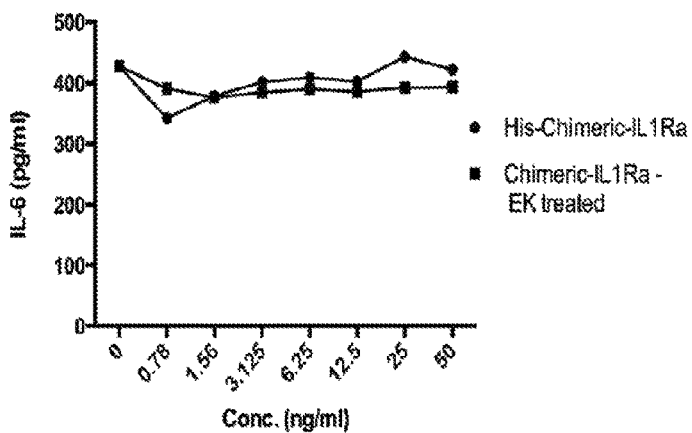

In order to determine the activity of recombinant IL-1Ra and chimeric-IL-1Ra, A549 cells were incubated with increasing concentrations of the proteins, as well as with commercial recombinant IL-1Ra (Anakinra), for 1 h before stimulation with IL-1β. Six hours later, IL-6 levels were measured in cell supernatants. Upon removal of the His tag linker, IL-1Ra exhibited comparable activity to Anakinra (FIGS. 1F and 9A-B). In contrast, chimeric-IL-1Ra lacked anti-IL-1 activity (FIGS. 1F and 9C-D).

Figure 2:
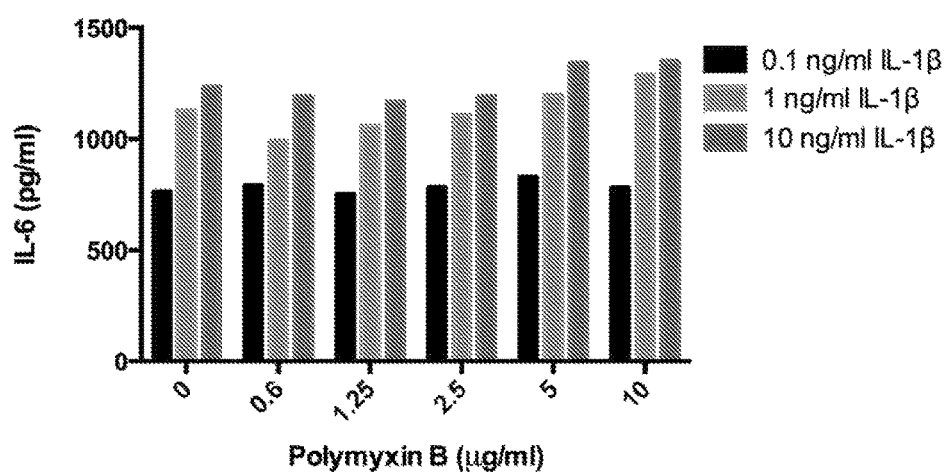
FIG. 2. Calibration of A549 IL-1 response assay. A549 cells were stimulated for 6 h with 0.1, 1 or 10 ng/ml recombinant IL-1b, either alone or with increasing doses of Polymyxin B. IL-6 levels were measured in the supernatants. IL-6 could not be detected in supernatants of A549 cells stimulated with 1 µg/ml LPS, either alone or together with Polymyxin B.
Figure 3A:
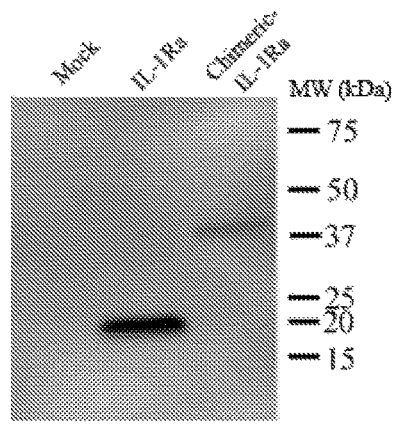
FIGS. 3A-C. Presents the expression of IL-1Ra and the chimera (IL-1beta-IL-1Ra chimera) coding vectors in HEK-T293 cells. (3A) A gel micrograph of a Western blot analysis. Anti-IL-1Ra antibody was used to detect IL-1Ra in lysed HEK-T293, that were transfected with either empty pCDNA3.1+ (Mock), IL-1Ra expressing vector (predicted Mw of 18 kDa) or chimeric-IL-1Ra expressing vector (predicted Mw of 37 kDa). (3B) A bar graph showing ELISA results. Lysates from HEK-T293 cells that were either mock transfected, transfected with IL-1Ra or chimeric-IL-1Ra were quantified. (3C) A549 cells were incubated for 1 h with lysates of mock transfected HEK-T293 cells, or transfectants containing 5 ng/ml IL-1Ra or 5 ng/ml chimeric-IL-1Ra, followed by 6 h of stimulation with IL-1b (0.1 ng/ml). Graph shows IL-6 levels in the cell supernatants (mean±SD, n=3, *p<0.05).
Figure 3B:
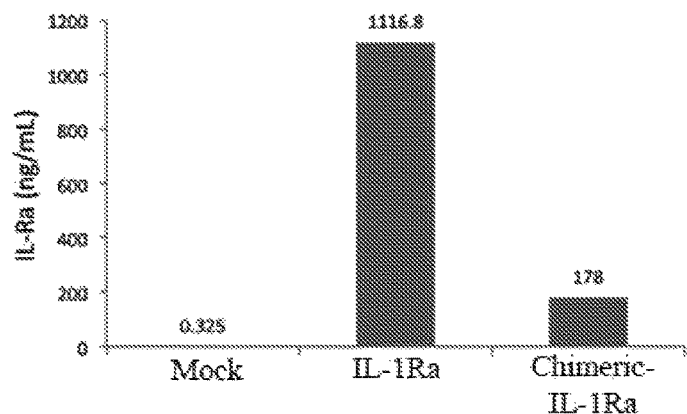
Figure 3C:
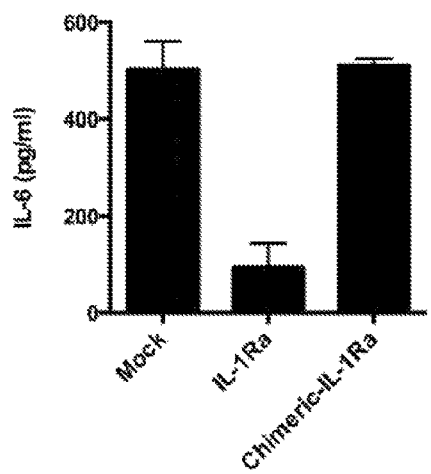
Figure 4:
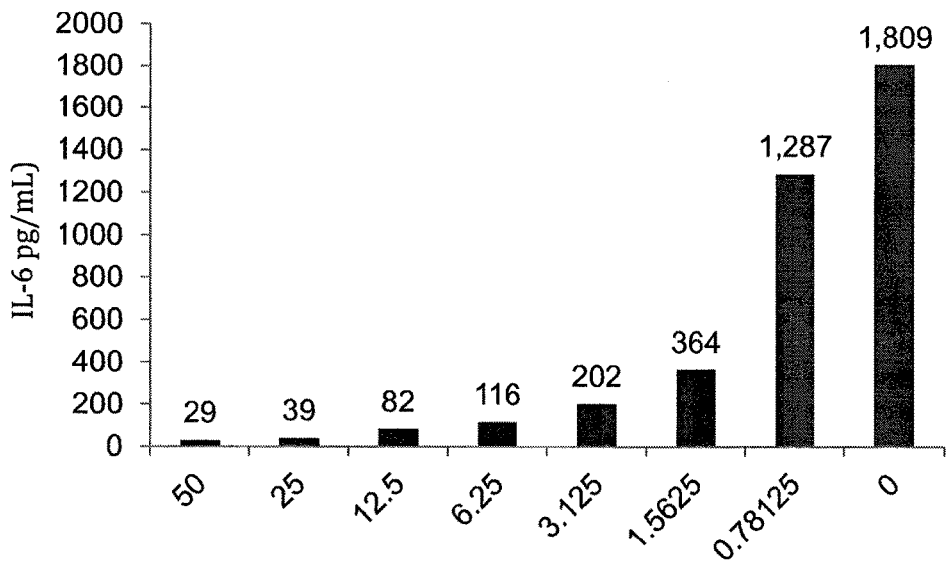
FIG. 4. Bar graphs showing calibration of the activity assay. A549 cells were incubated with recombinant IL-1Ra (serial dilutions from 50 ng/ml) for 1 h, followed by stimulated with IL-1β (0.1 ng/ml) for 6 hours. IL-6 levels in supernatants were determined and are indicated above each bar.
Figure 5A:
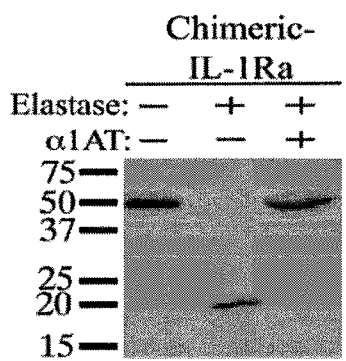
FIGS. 5A-E. Elastase cleavage of the chimeric-IL-1Ra endows it with IL-1 inhibition activity, while α1AT prevents it. (5A) Western blot, using anti-IL-1Ra antibody, of chimeric-IL-1Ra untreated, treated with elastase (50 µg/ml, 37° C. for 10 min) or treated with elastase and α1-antitrypsin (α1AT; 0.5 µg/ml). (5B) IL-6 levels after pre-incubation of 1 h with 15 ng/ml chimeric-IL-1Ra either untreated or treated with elastase or elastase and α1-antitrypsin (α1AT; 0.5 µg/ml) together followed by 6 h of 0.1 ng/ml IL-1 stimulation of A549 cells. ND—not detected. ***P<0.001 (mean±SD, n=4), NS—non significant. (5C) Western blot analysis using anti-IL-1Ra antibody of lysates that were obtained from HEK-T293 cells that were transfected with either IL-1Ra or chimeric-IL-1Ra. Chimeric-IL-1Ra containing lysates were treated with elastase (40 g/ml, 10 min at 37° C.). (5D) Lysates from mock-transfected HEK-T293 cells, either alone or pretreated with elastase, and lysates from chimeric-IL-1Ra-transfected HEK-T293 cells, either alone or pretreated with elastase, were assayed for IL-1-antagonistic activity. Graphs shows log 2 fold change of IL-6 levels following addition of elastase compared to untreated lysates (n=4). (5E) Different chimeric-IL-1Ra and elastase concentrations were used for dose-response treatment of A549 cells. The chimeric-IL-1Ra recombinant protein was digested with elastase (37° C., 10 min) then the reactions were added to the A549 cells for 1 h before stimulation with IL-1 (0.1 ng/ml) for further 6 h. The supernatants were collected and IL-6 levels were measured by ELISA (mean±SD, n=4).
Figure 5B:
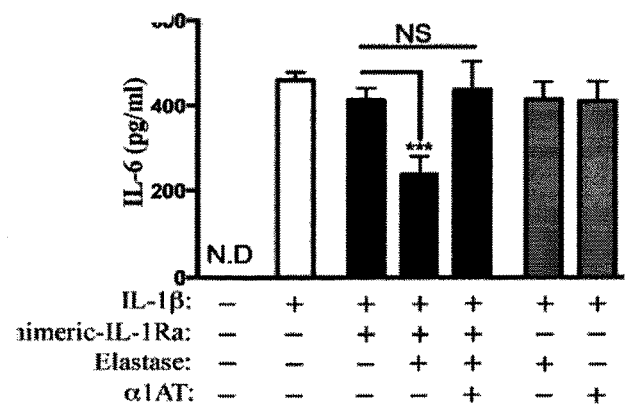
Figure 5C:
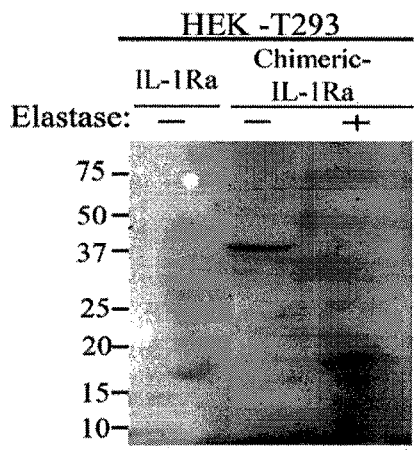
Figure 5D:
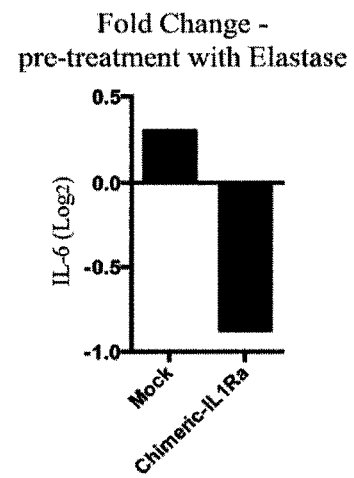
Figure 5E:
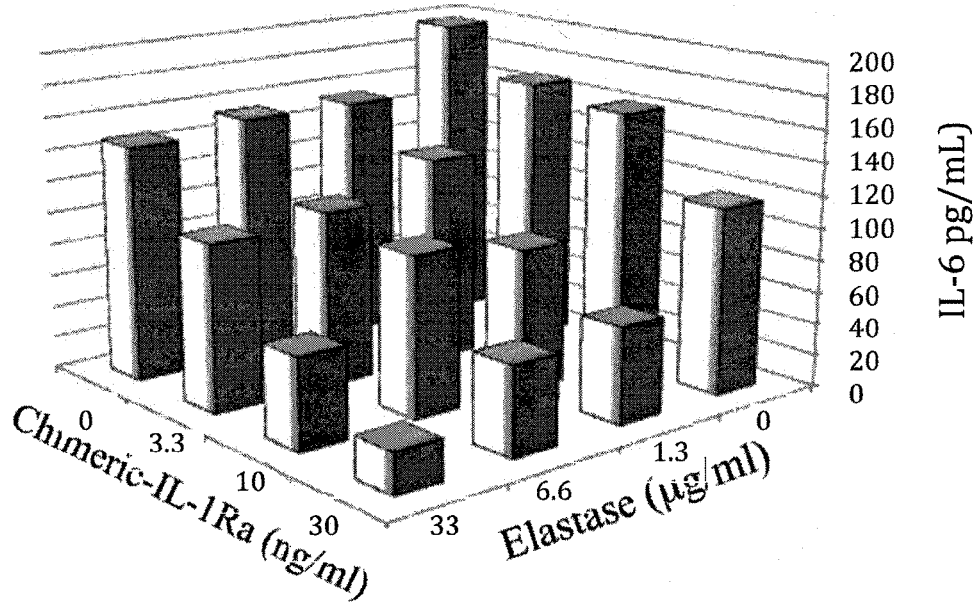
Figure 6A:
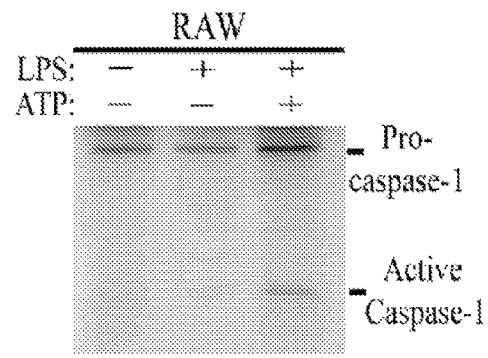
FIGS. 6A-C. Macrophage-derived proteases cleave the chimeric-IL-1Ra into mature form. (6A) Raw264.7 cells were either untreated, treated with LPS or LPS followed by ATP, and lysates were analyzed for caspase-1 activation by Western blot. (6B) Left, chimeric-IL-1Ra was incubated with control medium or with medium collected from RAW264.7 cells culture described in section A (37° C., 16 h) and analyzed by anti-IL1Ra Western blot. Right, chimeric-IL-1Ra lacking residues 102-120 (chimeric-IL-1Ra$^{\Delta 102-120}$) was incubated with control medium or with medium collected from LPS+ATP treated RAW264.7 and was analyzed by anti-IL-1Ra Western blot. (6C) Left, anti-IL-1Ra Western blot of chimeric-IL-1Ra cleavage (up to 60 min) by LPS-stimulated RAW264.7 cell lysates. Right, 16 h cleavage was performed with chimeric-IL-1Ra$^{\Delta 102-120}$.
Figure 6B:
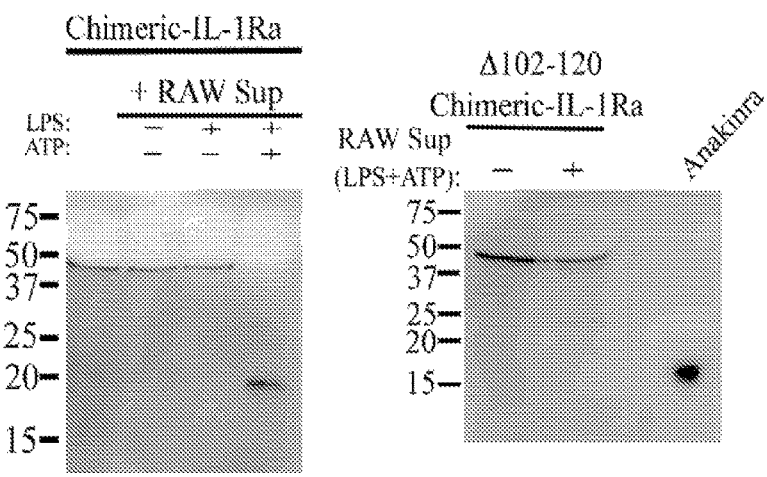
Figure 6C:
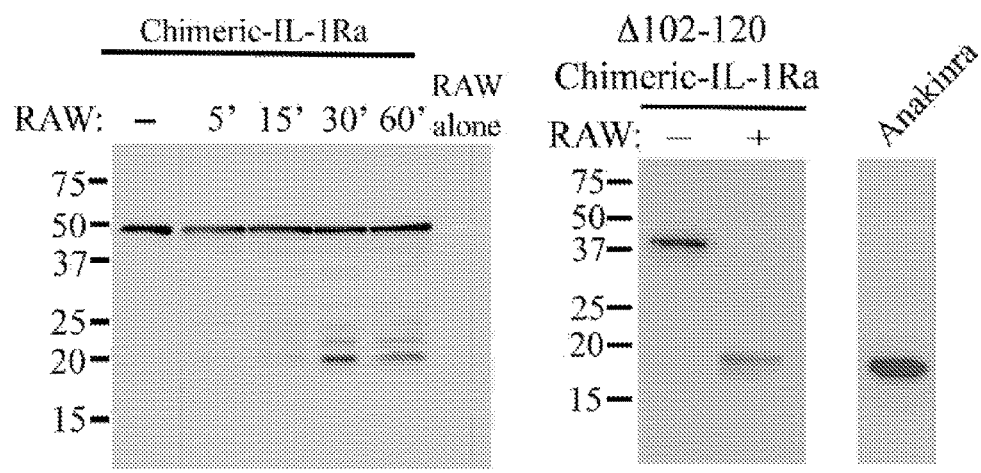

In order to exclude LPS contamination, sensitivity of A549 cells to LPS was confirmed to be negative, and introduction of polymyxin B yielded no change in IL-1-induced IL-6 levels (FIG. 2).

Example 2

Expression of the Chimeric-IL-1Ra in Bacterial and HEK-T293 Cells

The pET30a-chimeric-IL-1Ra vector was used to express the protein in bacterial cells. The bacterial cells were transformed, grown to logarithmic phase, induced with IPTG and lysed using sonication. The lysates were used in order to isolate the His tagged-protein with Ni-NTA beads (FIG. 1E).

A non-bacterial expression system was used in order to test whether the joining of IL-1beta propeptide to IL-1Ra (chimeric-IL-1Ra) will inhibit the binding to IL-1R1. HEK-T293 cells were transfected with the construct encoding the chimeric-IL-1Ra vector, along with transfections of IL-1Ra alone or with empty vector. The cells were cultured for 24 hours (h) and lysates were prepared. In order to test whether translation of this molecule is feasible, and the protein is stable, cell lysates were analyzed for IL-1Ra by Western blot and ELISA (FIG. 3A-B). Indeed, the chimeric molecule was detected by anti-IL-1Ra antibodies both in western blot and by ELISA. According to the expectations, IL-1Ra alone was found to be, approximately, 18 kDa and the additional IL-1β propeptide resulted in a protein of 38 kDa in size. In mock-transfected cells endogenous IL-1Ra was detectable neither by western blot nor by ELISA, thus it was concluded that the existence of IL-1Ra in the transfected cells was indeed due to the chimeric-IL-1Ra, or the IL-1Ra only, encoding vectors.

In order to confirm that the lysates also contained the related expected activities, equal amounts of either mock-transfected, IL-1Ra or chimeric-IL-1Ra transfected cell lysates were added to A549 cells, 1 h before addition of IL-1β. Six hours later, IL-6 levels were determined in the supernatants. HEK-T293-derived IL-1Ra inhibited IL-1 activity in A549 cells, while the chimeric-IL-1Ra was comparable to mock-transfected cell lysates in that it lacked anti-IL-1 activity (FIG. 3C).

Example 3

Chimeric-IL-1Ra does not Inhibit IL-1 Stimulation

In order to estimate the bioactivity of the chimeric-IL-1Ra molecule it was compared to IL-1Ra for the ability to occupy IL-1R1 (the receptor) and inhibit IL-1beta stimulation. A549 cells, which respond to IL-1β stimulation by secretion of IL-6, were used as a system to test inhibition of IL-1β binding to IL-1R1. Pre-incubation of decreasing doses of recombinant IL-1Ra to the cells 1 h prior to IL-1β resulted in a dose-dependent response of IL-6, demonstrating the sensitivity of these cells to IL-1Ra inhibition of IL-1β (FIG. 4).

Addition of cell lysates obtained from HEK-T293 transfected with mock, IL-1Ra alone or chimeric IL-1beta-IL-1Ra showed that only IL-1Ra and not chimeric-IL-1Ra, is capable of inhibiting IL-1β stimulation and lowering the IL-6 response from the A549 cells (FIG. 3C).

The chimeric-IL-1Ra transfected cell lysate did not inhibit IL-1β mediated IL-6 response, and was comparable to pre-incubation with the mock-transfected cell lysate. Therefore it was concluded that the N-terminal of the chimeric-IL-1Ra-IL-1β (the portion of the IL-1β propeptide) interferes with the protein's ability to bind and occupy IL-1R1 on A549 cells.

Example 4

Chimeric-IL-1Ra Molecule is Processed by Elastase into Active IL-1Ra

In order for the chimera to obtain IL-1Ra inhibitory activity, the N-terminal portion of the protein must be cleaved off during the inflammation. The chimera contains multiple sites for proteolysis at the end of the IL-1β propeptide side of the chimera (FIG. 1C-D).

Thus it was important to test the digestibility of the chimera in the presence of inflammatory enzymes. Chimeric-IL-1Ra was incubated with elastase and resulting products were analyzed by Western blot with antibody specific for IL-1Ra. As shown in FIG. 5A, chimeric-IL-1Ra is cleaved to form a ~20 kDa fragment, comparable in size to IL-1Ra. The cleavage is inhibited by alpha-1 antitrypsin (α1AT), an inhibitor of elastase.

In order to examine whether the cleaved product contain IL-1Ra activity, A549 cells were incubated with the products of the enzymatic reaction, 1 h before IL-1β stimulation. According to IL-6 levels in the supernatants, elastase-treated chimeric-IL-1Ra blocks IL-1 in cell medium (FIG. 5B). Similar results were obtained with HEK-T293-derived chimeric-IL-1Ra (FIG. 5C). To test whether elastase cleavage of the chimera results in the formation of IL-1R1 blocking peptide, A549 cells were pre-incubated with lysates of the mock or the chimera transfected cells that were digested with elastase prior to the stimulation with IL-1beta. Levels of IL-6 secreted by A549 cells showed that the addition of elastase to mock-transfected cell lysate caused an increase in the IL-6 secretion; however addition of elastase to the chimera lysate, resulted in lower IL-6 levels (FIG. 5D), suggesting that elastase could cut off the chimeric-IL-1Ra, thus transforming the inactive chimera to at least two peptides, wherein at least one peptide possesses anti-inflammatory activity.

Furthermore, antagonizing capacity of chimeric-IL-1Ra correlated with the levels of the inflammatory protease, elastase (FIG. 5E), exhibiting maximal inhibition of IL-1 with higher concentration of chimeric-IL-1Ra together with excessive concentrations of elastase.

Example 5

Exposure of Chimeric-IL-1Ra to Activated RAW264.7 Cells Results in Release of Active IL-1Ra In order to examine whether enzymatic products released from stimulated macrophages can activate chimeric-IL-1Ra, RAW264.7 cells were stimulated with either LPS alone, or together with ATP and activation of caspase-1 was confirmed by Western blot analysis (FIG. 6A). Supernatants were then collected and applied to chimeric-IL-1Ra for 16 h. According to Western blot analysis (FIG. 6B), chimeric-IL-1Ra was cleaved into IL-1Ra by products that were released from activated RAW264.7 cells.

In order to confirm the requirement of protease cleavage sites, a deletion-mutation was generated (chimeric-IL-1Ra$^{\Delta 102-120}$), which lacks established protease target sites. Indeed, as shown in FIG. 6B, chimeric-IL-1Ra$^{\Delta 102-120}$ displayed decreased levels of IL-1Ra release by exposure to supernatants from activated RAW264.7.

Lysates of RAW264.7 cells also cleaved chimeric-IL-1Ra (FIG. 7D). As shown, LPS-activation was sufficient to elicit a proteolytic lysate. In addition, activation was not absent when applied to chimeric-IL-1Ra$^{\Delta 102-120}$.

Example 6

Importance of Chimeric-IL-1Ra Residues 1-70

Figure 9E:
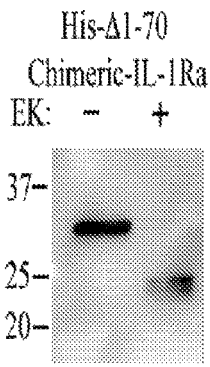
Figure 9F:
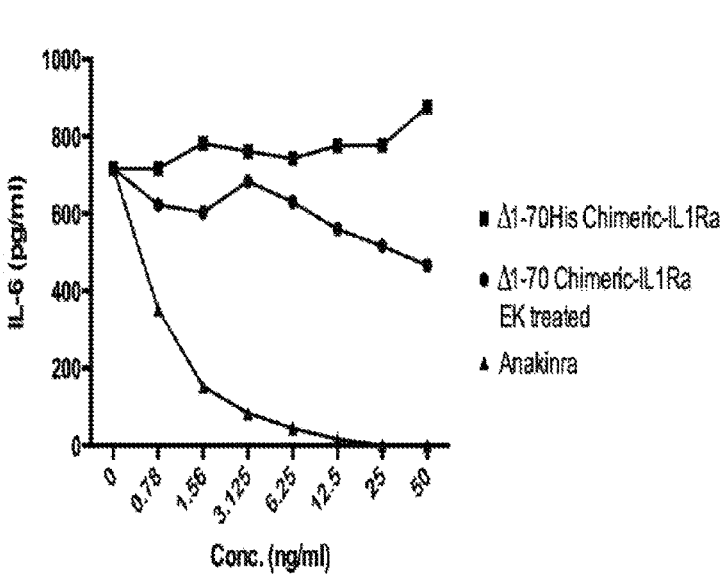

The precursor of IL-1β was shown to have a trypsin binding site that can result in a shorter precursor protein with decreased inhibitory activity compared to the active mature form of the precursor. Western blot analysis of the chimera revealed a major form of 38.9 kDa. However, a smaller form, of about 29.5 kDa was also observed (FIG. 7A). Thus, a chimeric-IL-1Ra$^{\Delta 1-70}$ was cloned and expressed in BL21 (DE3) bacterial cells (FIG. 7B). Chimeric-IL-1Ra$^{\Delta 1-70}$ was digested from the His-tag and linker (FIG. 9E) and its activity was determined using A549 cells (FIG. 9F and FIG. 7C). As shown in FIG. 7D, chimeric-IL-1Ra$^{\Delta 1-70}$ still served as an inactive chimera. However, some degradation products were observed, suggesting that the 70 residues in the N-terminal portion of the chimera may have a role in protein stability Example 7

Chimeric-IL-1Ra can be Activated In Vivo

Figure 8A:
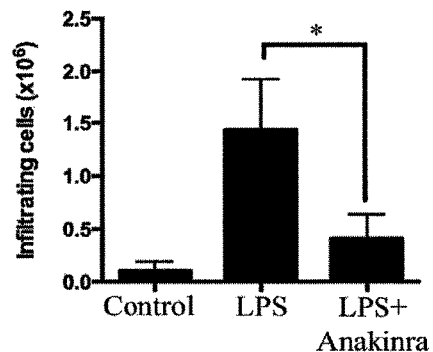
FIGS. 8A-C. Chimeric-IL-1Ra reduces infiltrating cells number following its activation in vivo (8A) Infiltrating cell numbers 24 h after the injection of Matrigel mixed with PBS alone, (n=3), 1 µg of LPS (n=3) or 1 µg LPS together with 1 µg Anakinra (n=7). *P<0.05. (8B) Infiltrating cell numbers 24 h and 48 h after the injection of Matrigel mixed with PBS, 1 µg LPS or 1 µg LPS together with 1 µg chimeric-IL-1Ra. Results are from multiple experiments, 24 h data shows: Control, n=3, LPS, n=4, LPS+chimeric-IL-1Ra, n=5. Data of 48 h shows: Control, n=4, LPS n=8, LPS+chimeric-IL-1Ra, n=8. ***P<0.001 of LPS vs LPS+chimeric-IL-1Ra group. (8C) Infiltrating cells in LPS-Matrigel plug model of inflammation are consisted of neutrophils. Flow cytometer analyses of GR1/Ly6G staining from CD11b gated cells, of 24 h or 48 h Infiltrating cells into Matrigel plugs, that were injected with 1 µg LPS with or without 1 chimeric-IL-1Ra.
Figure 8B:
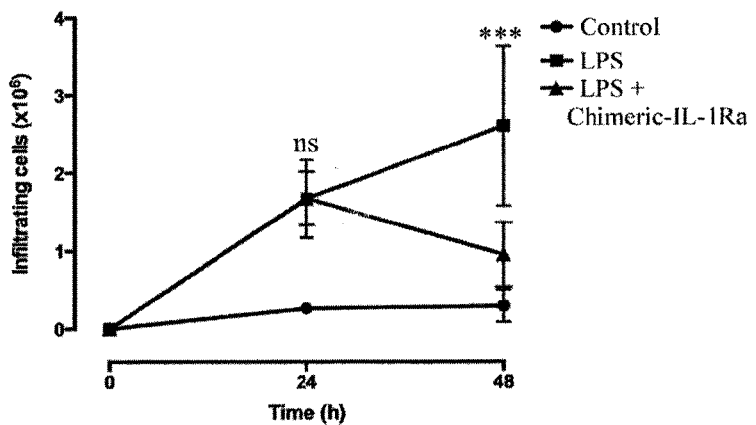
Figure 8C:
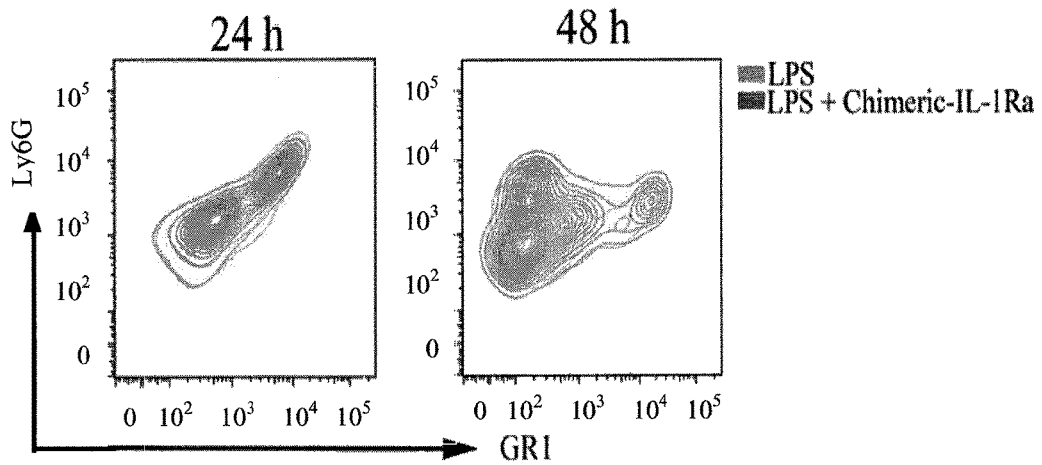

In order to test activation of chimeric-IL-1Ra in an animal model that is primarily comprised of an inflammatory component, sterile Matrigel was supplemented with 1 μg of LPS and either Anakinra or chimeric-IL-1Ra. Matrigel plugs were then implanted under the skin of wild-type mice. After 24 or 48 hours, plugs were collected and the cellular infiltrate isolated and quantified. As shown in FIG. 8A, addition of Anakinra to the Matrigel reduced 24-hr infiltrates, while addition of chimeric-IL-1Ra did not alter 24-hr infiltrates. However, following 48 hours from the injection of plugs, reduced numbers of infiltrating cells were observed (FIG. 8B). As demonstrated by FACS analysis, infiltrating cells were comprised of GR1+/Ly6G+ myeloid cells (FIG. 8C), suggesting chimeric-IL-1Ra requires neutrophil-derived enzymes in order to be activated at an inflammatory site.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

What is claimed is:

1. A fusion protein comprising a fragment derived from an IL-1beta propeptide with a C-terminal protease cleavage site, and an IL-1Ra mature peptide, wherein said fragment comprises the C-terminal protease cleavage site, and the IL-1Ra mature peptide is inactive as a part of the fusion protein.

2. The fusion protein of claim 1, further comprising a linker, wherein the carboxy terminus of said linker is attached to the amino terminus of said IL-1Ra mature peptide, and the amino terminus of said linker is attached to the carboxy terminus of said IL-1beta propeptide fragment.

3. The fusion protein of claim 2, wherein said linker comprises an amino acid pair of Lys-Leu.

4. The fusion protein of claim 1, wherein said fragment comprises at least 35 contiguous amino acid residues of the IL-1beta propeptide.

5. The fusion protein of claim 1, wherein said fragment comprises the amino acid sequence of SEQ ID NO:13.

6. The fusion protein of claim 1, wherein said fragment comprises the amino acid sequence of SEQ ID NO:9.

7. The fusion protein of claim 1, wherein said fragment comprises the amino acid sequence of SEQ ID NO:1.

8. The fusion protein of claim 1, wherein said IL-1Ra mature peptide comprises the amino acid sequence of SEQ ID NO:2.

9. The fusion protein of claim 1, comprising the amino acid sequence of SEQ ID NO: 3.

10. The fusion protein of claim 1, comprising the amino acid sequence of SEQ ID NO: 10.

11. A pharmaceutical composition comprising the protein of claim 1 and a carrier.

12. A method of treating an IL-1 associated disease or disorder in a subject in need thereof, the method comprising the step of administering to said subject a therapeutically effective amount of the pharmaceutical composition of claim 11.

13. The method of claim 12, wherein the IL-1 associated disease or disorder is an inflammatory disease or disorder.

14. A method for inhibiting or reducing inflammation in a subject in need thereof, comprising the step of administering to said subject a therapeutically effective amount of the pharmaceutical composition of claim 11.

15. A polynucleotide comprising (a) the nucleic acid sequences of SEQ ID NO: 4 and SEQ ID NO: 5; or (b) the nucleic acid sequence of SEQ ID NO: 6.

16. A polynucleotide, comprising (a) the nucleic acid sequences of SEQ ID NO: 11 and SEQ ID NO: 5; or (b) the nucleic acid sequence of SEQ ID NO: 12.

17. An expression vector comprising the polynucleotide of claim 15 or 16.

18. An isolated cell comprising the expression vector of claim 17.

* * * * *

SEQUENCE LISTING

```
<160> NUMBER OF SEQ ID NOS: 24

<210> SEQ ID NO 1
<211> LENGTH: 120
<212> TYPE: PRT
<213> ORGANISM: Homo sapiens

<400> SEQUENCE: 1

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg
        115                 120

<210> SEQ ID NO 2
<211> LENGTH: 152
<212> TYPE: PRT
<213> ORGANISM: Homo sapiens

<400> SEQUENCE: 2
```

```
Arg Pro Ser Gly Arg Lys Ser Lys Met Gln Ala Phe Arg Ile Trp
1               5                   10                  15

Asp Val Asn Gln Lys Thr Phe Tyr Leu Arg Asn Asn Gln Leu Val Ala
            20                  25                  30

Gly Tyr Leu Gln Gly Pro Asn Val Asn Leu Glu Glu Lys Ile Asp Val
            35                  40                  45

Val Pro Ile Glu Pro His Ala Leu Phe Leu Gly Ile His Gly Gly Lys
    50                  55                  60

Met Cys Leu Ser Cys Val Lys Ser Gly Asp Glu Thr Arg Leu Gln Leu
65                  70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
                100                 105                 110

Ser Ala Ala Cys Pro Gly Trp Phe Leu Cys Thr Ala Met Glu Ala Asp
            115                 120                 125

Gln Pro Val Ser Leu Thr Asn Met Pro Asp Glu Gly Val Met Val Thr
    130                 135                 140

Lys Phe Tyr Phe Gln Glu Asp Glu
145                 150

<210> SEQ ID NO 3
<211> LENGTH: 274
<212> TYPE: PRT
<213> ORGANISM: Artificial
<220> FEATURE:
<223> OTHER INFORMATION: Synthetic

<400> SEQUENCE: 3

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Lys Leu Arg Pro Ser Gly Arg Lys
            115                 120                 125

Ser Ser Lys Met Gln Ala Phe Arg Ile Trp Asp Val Asn Gln Lys Thr
    130                 135                 140

Phe Tyr Leu Arg Asn Asn Gln Leu Val Ala Gly Tyr Leu Gln Gly Pro
145                 150                 155                 160

Asn Val Asn Leu Glu Glu Lys Ile Asp Val Val Pro Ile Glu Pro His
                165                 170                 175

Ala Leu Phe Leu Gly Ile His Gly Gly Lys Met Cys Leu Ser Cys Val
            180                 185                 190

Lys Ser Gly Asp Glu Thr Arg Leu Gln Leu Glu Ala Val Asn Ile Thr
    195                 200                 205
```

Asp Leu Ser Glu Asn Arg Lys Gln Asp Lys Arg Phe Ala Phe Ile Arg
            210                 215                 220

Ser Asp Ser Gly Pro Thr Thr Ser Phe Glu Ser Ala Ala Cys Pro Gly
225                 230                 235                 240

Trp Phe Leu Cys Thr Ala Met Glu Ala Asp Gln Pro Val Ser Leu Thr
                245                 250                 255

Asn Met Pro Asp Glu Gly Val Met Val Thr Lys Phe Tyr Phe Gln Glu
            260                 265                 270

Asp Glu

<210> SEQ ID NO 4
<211> LENGTH: 360
<212> TYPE: DNA
<213> ORGANISM: Homo sapiens

<400> SEQUENCE: 4

```
atggcagaag tacctgagct cgccagtgaa atgatggctt attacagtgg caatgaggat    60
gacttgttct ttgaagctga tgccctaaa cagatgaagt gctccttcca ggacctggac    120
ctctgccctc tggatggcgg catccagcta cgaatctccg accaccacta cagcaagggc    180
ttcaggcagg ccgcgtcagt tgttgtggcc atggacaagc tgaggaagat gctggttccc    240
tgcccacaga ccttccagga gaatgacctg agcaccttct ttcccttcat ctttgaagaa    300
gaacctatct tcttcgacac atgggataac gaggcttatg tgcacgatgc acctgtacga    360
```

<210> SEQ ID NO 5
<211> LENGTH: 459
<212> TYPE: DNA
<213> ORGANISM: Homo sapiens

<400> SEQUENCE: 5

```
cgaccctctg ggagaaaatc agcaagatg caagccttca gaatctggga tgttaaccag    60
aagaccttct atctgaggaa caaccaacta gttgctggat acttgcaagg accaaatgtc    120
aatttagaag aaaagataga tgtggtaccc attgagcctc atgctctgtt cttgggaatc    180
catggaggga gatgtgcct gtcctgtgtc aagtctggtg atgagaccag actccagctg    240
gaggcagtta acatcactga cctgagcgag aacagaaagc aggacaagcg cttcgccttc    300
atccgctcag acagtggccc caccaccagt tttgagtctg ccgcctgccc cggttggttc    360
ctctgcacag cgatggaagc tgaccagccc gtcagcctca ccaatatgcc tgacgaaggc    420
gtcatggtca ccaaattcta cttccaggag gacgagtag    459
```

<210> SEQ ID NO 6
<211> LENGTH: 825
<212> TYPE: DNA
<213> ORGANISM: Artificial
<220> FEATURE:
<223> OTHER INFORMATION: Synthetic

<400> SEQUENCE: 6

```
atggcagaag tacctgagct cgccagtgaa atgatggctt attacagtgg caatgaggat    60
gacttgttct ttgaagctga tgccctaaa cagatgaagt gctccttcca ggacctggac    120
ctctgccctc tggatggcgg catccagcta cgaatctccg accaccacta cagcaagggc    180
ttcaggcagg ccgcgtcagt tgttgtggcc atggacaagc tgaggaagat gctggttccc    240
tgcccacaga ccttccagga gaatgacctg agcaccttct ttcccttcat ctttgaagaa    300
gaacctatct tcttcgacac atgggataac gaggcttatg tgcacgatgc acctgtacga    360
```

```
aagcttcgac cctctgggag aaaatccagc aagatgcaag ccttcagaat ctgggatgtt    420
aaccagaaga ccttctatct gaggaacaac caactagttg ctggatactt gcaaggacca    480
aatgtcaatt tagaagaaaa gatagatgtg gtacccattg agcctcatgc tctgttcttg    540
ggaatccatg gagggaagat gtgcctgtcc tgtgtcaagt ctggtgatga accagactc     600 cagctggagg cagttaacat cactgacctg agcgagaaca gaaagcagga caagcgcttc    660
gccttcatcc gctcagacag tggccccacc accagttttg agtctgccgc ctgccccggt    720
tggttcctct gcacagcgat ggaagctgac cagcccgtca gcctcaccaa tatgcctgac    780
gaaggcgtca tggtcaccaa attctacttc caggaggacg agtag                    825
```

```
<210> SEQ ID NO 7
<211> LENGTH: 153
<212> TYPE: PRT
<213> ORGANISM: Homo sapiens

<400> SEQUENCE: 7

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140

Asp Phe Thr Met Gln Phe Val Ser Ser
145                 150
```

```
<210> SEQ ID NO 8
<211> LENGTH: 269
<212> TYPE: PRT
<213> ORGANISM: Homo sapiens

<400> SEQUENCE: 8

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
```

```
                    85                  90                  95
Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
        130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
                180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
        210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 9
<211> LENGTH: 50
<212> TYPE: PRT
<213> ORGANISM: Homo sapiens

<400> SEQUENCE: 9

Met Asp Lys Leu Arg Lys Met Leu Val Pro Cys Pro Gln Thr Phe Gln
1               5                   10                  15

Glu Asn Asp Leu Ser Thr Phe Phe Pro Phe Ile Phe Glu Glu Glu Pro
            20                  25                  30

Ile Phe Phe Asp Thr Trp Asp Asn Glu Ala Tyr Val His Asp Ala Pro
        35                  40                  45

Val Arg
    50

<210> SEQ ID NO 10
<211> LENGTH: 204
<212> TYPE: PRT
<213> ORGANISM: Artificial
<220> FEATURE:
<223> OTHER INFORMATION: Synthetic

<400> SEQUENCE: 10

Met Asp Lys Leu Arg Lys Met Leu Val Pro Cys Pro Gln Thr Phe Gln
1               5                   10                  15

Glu Asn Asp Leu Ser Thr Phe Phe Pro Phe Ile Phe Glu Glu Glu Pro
            20                  25                  30

Ile Phe Phe Asp Thr Trp Asp Asn Glu Ala Tyr Val His Asp Ala Pro
        35                  40                  45

Val Arg Lys Leu Arg Pro Ser Gly Arg Lys Ser Ser Lys Met Gln Ala
    50                  55                  60

Phe Arg Ile Trp Asp Val Asn Gln Lys Thr Phe Tyr Leu Arg Asn Asn
65                  70                  75                  80
```

```
Gln Leu Val Ala Gly Tyr Leu Gln Gly Pro Asn Val Asn Leu Glu Glu
                85                  90                  95
Lys Ile Asp Val Val Pro Ile Glu Pro His Ala Leu Phe Leu Gly Ile
            100                 105                 110
His Gly Gly Lys Met Cys Leu Ser Cys Val Lys Ser Gly Asp Glu Thr
        115                 120                 125
Arg Leu Gln Leu Glu Ala Val Asn Ile Thr Asp Leu Ser Glu Asn Arg
    130                 135                 140
Lys Gln Asp Lys Arg Phe Ala Phe Ile Arg Ser Asp Ser Gly Pro Thr
145                 150                 155                 160
Thr Ser Phe Glu Ser Ala Ala Cys Pro Gly Trp Phe Leu Cys Thr Ala
                165                 170                 175
Met Glu Ala Asp Gln Pro Val Ser Leu Thr Asn Met Pro Asp Glu Gly
            180                 185                 190
Val Met Val Thr Lys Phe Tyr Phe Gln Glu Asp Glu
        195                 200
```

```
<210> SEQ ID NO 11
<211> LENGTH: 150
<212> TYPE: DNA
<213> ORGANISM: Homo sapiens

<400> SEQUENCE: 11
atggacaagc tgaggaagat gctggttccc tgcccacaga ccttccagga gaatgacctg      60
agcaccttct ttcccttcat ctttgaagaa gaacctatct tcttcgacac atgggataac     120
gaggcttatg tgcacgatgc acctgtacga                                      150

<210> SEQ ID NO 12
<211> LENGTH: 615
<212> TYPE: DNA
<213> ORGANISM: Artificial
<220> FEATURE:
<223> OTHER INFORMATION: Synthetic

<400> SEQUENCE: 12
atggacaagc tgaggaagat gctggttccc tgcccacaga ccttccagga gaatgacctg      60
agcaccttct ttcccttcat ctttgaagaa gaacctatct tcttcgacac atgggataac     120
gaggcttatg tgcacgatgc acctgtacga aagcttcgac cctctgggag aaaatccagc     180
aagatgcaag ccttcagaat ctgggatgtt aaccagaaga ccttctatct gaggaacaac     240
caactagttg ctggatactt gcaaggacca aatgtcaatt tagaagaaaa gatagatgtg     300
gtacccattg agcctcatgc tctgttcttg ggaatccatg gagggaagat gtgcctgtcc     360
tgtgtcaagt ctggtgatga gaccagactc cagctggagg cagttaacat cactgacctg     420
agcgagaaca gaaagcagga caagcgcttc gccttcatcc gctcagacag tggccccacc     480
accagttttg agtctgccgc ctgccccggt tggttcctct gcacagcgat ggaagctgac     540
cagcccgtca gcctcaccaa tatgcctgac gaaggcgtca tggtcaccaa attctacttc     600
caggaggacg agtag                                                     615

<210> SEQ ID NO 13
<211> LENGTH: 19
<212> TYPE: PRT
<213> ORGANISM: Homo sapiens

<400> SEQUENCE: 13
```

```
Pro Ile Phe Phe Asp Thr Trp Asp Asn Glu Ala Tyr Val His Asp Ala
1               5                   10                  15

Pro Val Arg
```

<210> SEQ ID NO 14
<211> LENGTH: 36
<212> TYPE: DNA
<213> ORGANISM: Artificial
<220> FEATURE:
<223> OTHER INFORMATION: Synthetic

<400> SEQUENCE: 14
cacggatccg ccaccatggc agaagtacct gagctc                       36

<210> SEQ ID NO 15
<211> LENGTH: 35
<212> TYPE: DNA
<213> ORGANISM: Artificial
<220> FEATURE:
<223> OTHER INFORMATION: Synthetic

<400> SEQUENCE: 15
cacaagcttt cgtacaggtg catcgtgcac ataag                        35

<210> SEQ ID NO 16
<211> LENGTH: 32
<212> TYPE: DNA
<213> ORGANISM: Artificial
<220> FEATURE:
<223> OTHER INFORMATION: Synthetic

<400> SEQUENCE: 16
cacaagcttc gaccctctgg gagaaaatcc ag                           32

<210> SEQ ID NO 17
<211> LENGTH: 37
<212> TYPE: DNA
<213> ORGANISM: Artificial
<220> FEATURE:
<223> OTHER INFORMATION: Synthetic

<400> SEQUENCE: 17
tcacagtgcg gccgcctact cgtcctcctg gaagtag                      37

<210> SEQ ID NO 18
<211> LENGTH: 40
<212> TYPE: DNA
<213> ORGANISM: Artificial
<220> FEATURE:
<223> OTHER INFORMATION: Synthetic

<400> SEQUENCE: 18
caggatccgc caccatgcga ccctctggga gaaaatccag                   40

<210> SEQ ID NO 19
<211> LENGTH: 22
<212> TYPE: DNA
<213> ORGANISM: Artificial
<220> FEATURE:
<223> OTHER INFORMATION: Synthetic

<400> SEQUENCE: 19
cgaccctctg ggagaaaatc ca                                      22

<210> SEQ ID NO 20

```
<211> LENGTH: 30
<212> TYPE: DNA
<213> ORGANISM: Artificial
<220> FEATURE:
<223> OTHER INFORMATION: Synthetic

<400> SEQUENCE: 20
ttcttcttca aagatgaagg gaaagaaggt                                        30

<210> SEQ ID NO 21
<211> LENGTH: 24
<212> TYPE: DNA
<213> ORGANISM: Artificial
<220> FEATURE:
<223> OTHER INFORMATION: Synthetic

<400> SEQUENCE: 21
atggacaagc tgaggaagat gctg                                              24

<210> SEQ ID NO 22
<211> LENGTH: 25
<212> TYPE: DNA
<213> ORGANISM: Artificial
<220> FEATURE:
<223> OTHER INFORMATION: Synthetic

<400> SEQUENCE: 22
gcagatcgtc tctgaatgga acagg                                             25

<210> SEQ ID NO 23
<211> LENGTH: 36
<212> TYPE: DNA
<213> ORGANISM: Artificial
<220> FEATURE:
<223> OTHER INFORMATION: Synthetic

<400> SEQUENCE: 23
cacggatcca tggacaagaa gctgaggaag atgctg                                 36

<210> SEQ ID NO 24
<211> LENGTH: 4
<212> TYPE: PRT
<213> ORGANISM: Homo sapiens

<400> SEQUENCE: 24

Tyr Val His Asp
1
```